US009725140B2

(12) United States Patent
Kryzak

(10) Patent No.: US 9,725,140 B2
(45) Date of Patent: *Aug. 8, 2017

(54) APPARATUS, SYSTEM, AND METHOD FOR REMEDIATION OF CONTAMINATION

(71) Applicant: Thomas J. Kryzak, Altamont, NY (US)

(72) Inventor: Thomas J. Kryzak, Altamont, NY (US)

(73) Assignee: Air & Earth LLC, Altamont, NY (US)

( * ) Notice: Subject to any disclaimer, the term of this patent is extended or adjusted under 35 U.S.C. 154(b) by 40 days.

This patent is subject to a terminal disclaimer.

(21) Appl. No.: 14/578,323

(22) Filed: Dec. 19, 2014

(65) Prior Publication Data

US 2015/0197428 A1 Jul. 16, 2015

Related U.S. Application Data

(60) Continuation of application No. 13/525,326, filed on Jun. 17, 2012, now Pat. No. 8,940,161, which is a (Continued)

(51) Int. Cl.
*B63B 35/32* (2006.01)
*B09C 1/00* (2006.01)
(Continued)

(52) U.S. Cl.
CPC ............. *B63B 35/32* (2013.01); *A01H 4/001* (2013.01); *B08B 9/0933* (2013.01); *B09C 1/00* (2013.01);
(Continued)

(58) Field of Classification Search
CPC ........... B63B 35/32; A01H 4/001; B09C 1/00; B09C 1/08; B63C 11/00; B63C 11/52;
(Continued)

(56) References Cited

U.S. PATENT DOCUMENTS 4,290,883 A * 9/1981 Sama .................... A01K 61/003
15/1.7
4,957,622 A * 9/1990 Mims .................... B01D 21/245
210/170.04
(Continued)

*Primary Examiner* — Fred Prince
(74) *Attorney, Agent, or Firm* — GFD Patents LLC; Gerald F. Dudding

(57) ABSTRACT

An apparatus, system and method for removing and treating contaminated materials on a bottom of a body of water and introducing growth packets to revitalize the treated bottom of the body of water. The structure may comprise a vessel with an open face. The vessel may be lowered down to the bottom of the body of water with the face facing down. As a result, the vessel and the bottom form an isolated space. The structure may comprise at least one agitating device(s) for stirring up the materials inside the vessel so as to form a mixture containing the sediment materials which in turn contain the contaminants. Multiple at least one pipe(s) may be coupled to the vessel for transporting the mixture out of the vessel for processing (filtering, treating with chemicals, etc.) so as to neutralize or eliminate the contaminants in the mixture. Then, the treated mixture can be returned to the inside of the vessel via the at least one pipe(s).

27 Claims, 20 Drawing Sheets

Related U.S. Application Data continuation of application No. 13/206,325, filed on Aug. 9, 2011, now Pat. No. 8,221,621, which is a division of application No. 11/573,551, filed as application No. PCT/US2005/027732 on Aug. 5, 2005, now Pat. No. 8,017,012, which is a continuation of application No. 10/918,257, filed on Aug. 13, 2004, now Pat. No. 7,264,713.

(60) Provisional application No. 60/504,608, filed on Sep. 22, 2003, provisional application No. 60/499,619, filed on Sep. 3, 2003.

(51) Int. Cl.

| | | |
|---|---|---|
| *E02F 7/00* | (2006.01) | |
| *B63C 11/00* | (2006.01) | |
| *C02F 1/00* | (2006.01) | |
| *A01H 4/00* | (2006.01) | |
| *B08B 9/093* | (2006.01) | |
| *B09C 1/08* | (2006.01) | |
| *B63C 11/52* | (2006.01) | |
| *C02F 3/32* | (2006.01) | |
| *E02F 3/88* | (2006.01) | |
| *E02F 3/90* | (2006.01) | |
| *E02F 3/92* | (2006.01) | |
| *C02F 1/58* | (2006.01) | |
| *E02B 3/02* | (2006.01) | |
| *C02F 101/36* | (2006.01) | |
| *C02F 103/00* | (2006.01) | |

(52) U.S. Cl.
CPC .............. *B09C 1/08* (2013.01); *B63C 11/00* (2013.01); *B63C 11/52* (2013.01); *C02F 1/001* (2013.01); *C02F 1/004* (2013.01); *C02F 1/008* (2013.01); *C02F 1/58* (2013.01); *C02F 3/327* (2013.01); *E02B 3/023* (2013.01); *E02F 3/885* (2013.01); *E02F 3/8841* (2013.01); *E02F 3/905* (2013.01); *E02F 3/9256* (2013.01); *C02F 2101/363* (2013.01); *C02F 2103/007* (2013.01); *C02F 2209/006* (2013.01); *C02F 2301/046* (2013.01); *C02F 2301/063* (2013.01); *Y02W 10/18* (2015.05); *Y10S 111/90* (2013.01)

(58) Field of Classification Search
CPC .... C02F 1/004; C02F 3/327; C02F 2101/363; C02F 2103/007; C02F 2209/006; C02F 2301/046; C02F 2301/063; C02F 1/001; C02F 1/58; C02F 1/008; E02F 3/8841; E02F 3/885; E02F 3/905; E02F 34/9256; E02B 3/023; Y10S 111/90; Y02W 10/18
USPC .... 210/167.01, 170.01, 170.04, 170.05, 602, 210/474; 405/128.1, 128.7; 37/307, 313, 37/318
See application file for complete search history.

(56) References Cited

U.S. PATENT DOCUMENTS

| | | | |
|---|---|---|---|
| 6,637,135 B2* | 10/2003 | Chesner | B01D 61/18 37/318 |
| 8,940,161 B2* | 1/2015 | Kryzak | A01H 4/001 210/167.01 |
| 2006/0051162 A1* | 3/2006 | Chesner | E02F 3/06 405/57 |

* cited by examiner

APPARATUS, SYSTEM, AND METHOD FOR REMEDIATION OF CONTAMINATION

BACKGROUND OF THE INVENTION

1. Technical Field

The present invention relates to cleaning toxic waste, and more particularly, to an apparatus, system and method for remediation of contaminated materials from a body of water.

2. Related Art

It has been found that some naturally occurring bodies of water such as lakes, reservoirs, rivers and streams have become contaminated with material, such as, for example, with chemicals such as polychlorinated biphenyls ("PCBs") or chlorinated dioxins.

There is a need for an apparatus, system and method for removal of these contaminated materials.

SUMMARY OF THE INVENTION

A first aspect of the present invention provides an apparatus for remediation of contaminated sediment at the bottom of a body of water, said apparatus comprising: a vessel having an opening facing and configured for direct physical contact with the bottom of the body of water so as to isolate an area contained within the opening from areas outside the opening; at least one agitator for suspending sediment contained within the opening; a mapping system for determining a longitudinal and latitudinal coordinates of the locations; first pipes configured to transport the contained and suspended sediment from the isolated area to the mapping system; and second pipes configured to transport processed suspended sediment from the mapping a processing system to the isolated area.

DETAILED DESCRIPTION OF THE INVENTION

Figure 1:
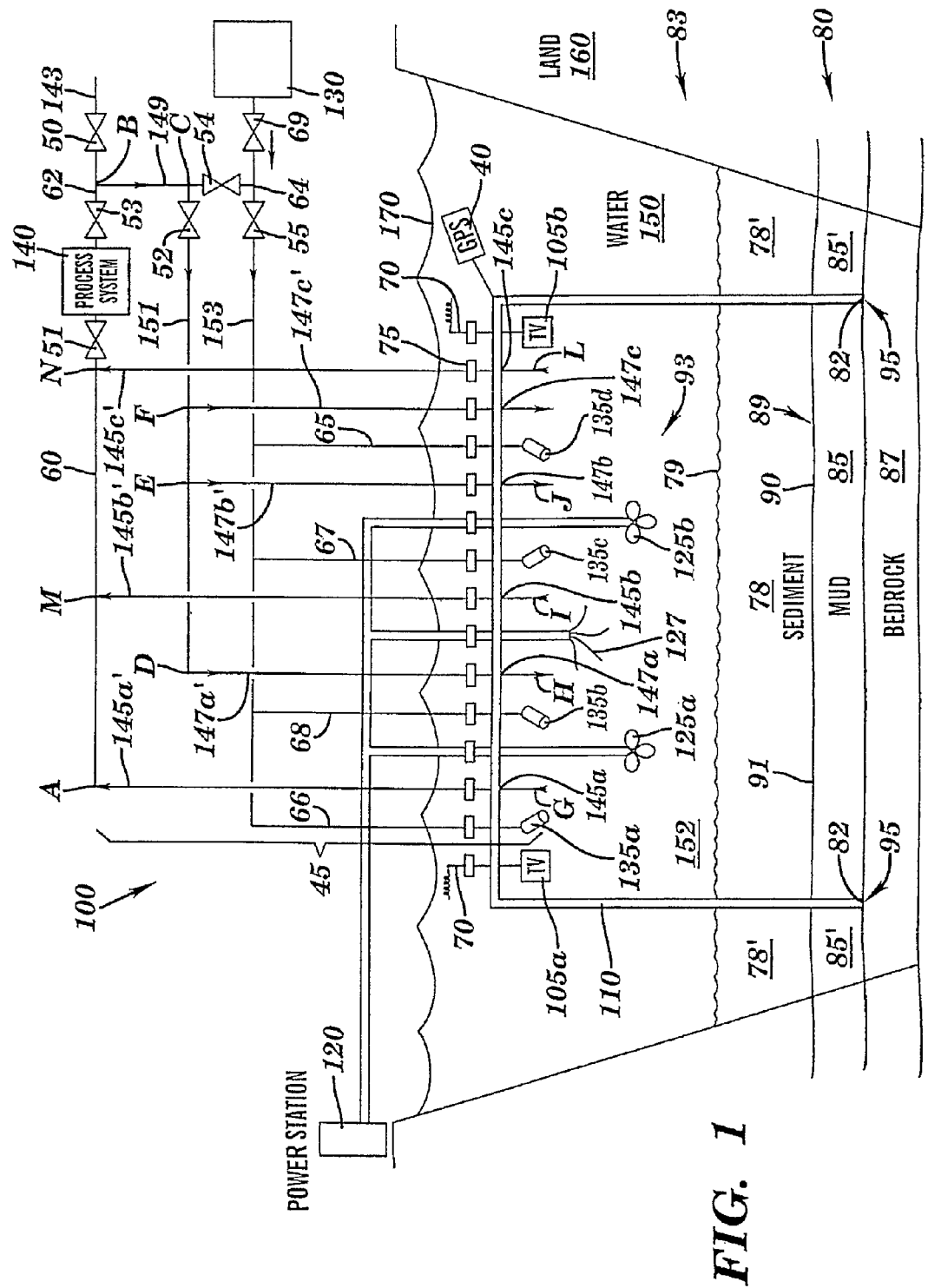
FIG. 1 illustrates an apparatus for removing and treating materials in a body of water, the apparatus comprising a vessel, according to embodiments of the present invention.

FIG. 1 illustrates an apparatus 100, such as a Closed Loop Extraction Lunch Box ("CLELB"), wherein an open side 90 of the apparatus 100 may be facing a bottom 80 of the body of water 83, and an edge 82 of a vessel 110 may be directly and physically in contact with the bottom 80 of the body of water 83, such that the contained water and suspended sediment 152, the contained precipitated sediment 78 and the contained mud 85 may be essentially completely isolated or separated from an uncontained area of water and suspended sediment 150, the precipitated sediment 78' and the uncontained mud 85' outside the vessel 110. The body of water 83 may include water and suspended sediment 150 and the bottom 80 of the body of water 83, wherein the bottom 80 of the body of water 83 may include sediment 78', mud 85' and bedrock 87 and may be adjacent to a body of land 160, such as, for example, a water along a shore, water along an edge of a river, water along an edge of a lakefront, or water along an edge of a beach. Alternatively, the edge 82 of the vessel 110 may be directly and physically in contact with the mud 85 and 85', such that the contained water and suspended sediment 152, contained precipitated sediment 78 and contained mud 85 may be essentially completely isolated or separated from the uncontained area of water and suspended sediment 150, the uncontained precipitated sediment 78' and the uncontained mud 85'. Alternatively, the edge 82 of the vessel 110 may be directly and physically in contact with the precipitated sediment 78 and 78', such that the contained water and suspended sediment 152 and contained precipitated sediment 78 may be essentially completely isolated or separated from the uncontained area of water and suspended sediment 150 and the uncontained precipitated sediment 78'. The contained precipitated sediment portion 78 and an uncontained precipitated sediment portion 78', may be, for example, contaminated material, the contained mud portion 85 and the uncontained mud portion 85' may be a mixture of earth and water so as to be adhesive, and the bedrock portion 87 may be rock, shale or other hard material that supports the mud, 85 and 85' and/or sediment, 78 and 78'. In some cases, some or all of the contained sediment portion 78 and uncontained sediment portion 78', and/or the contained mud portion 85 and the uncontained mud portion 85' of the bottom 80 of the body of water 83 may contain levels of chemical contamination, such that the levels of chemical contamination may be unhealthful or toxic to people, wildlife, such as fish, or plant life living in the body of water 83. The chemical contamination may be heavy metals such as mercury, lead, or other metals such as chromium, magnesium, manganese, copper, or organics, such as polychlorinated biphenyls (PCB's), dioxins, or halogenated or aromatic solvents such as trichloroethylene, toluene or benzene. Said levels may be as low as 0 to 100 parts per trillion by weight, for example, or at the minimum detection limit of modern analytical instruments for quantifying the level of chemical contamination. In cases for which the levels of contamination may be unhealthful or toxic, it may be desirable or necessary to remove the chemically contaminated portions from the bottom 80 using the apparatus 100 as depicted in FIG. 1.

The vessel 110 may comprise: viewing devices 105a and 105b, such as waterproof cameras, may be used to display the contained area 93. The vessel 110 may be a compartment-box or any other appropriate container having waterproof walls. The vessel 110 may be made of rigid material such as plastic, rubber or metal. Alternatively, the vessel 110 may be made of flexible material such as flexible rubber. The vessel 110 may have any appropriate solid geometric shape such as polygon, cubic, cylindrical, spherical, pyramidal, rhomboid or conical. Conduits 70 may house coaxial cables or other appropriate wiring to supply the viewing devices 105a and 105b with electricity and to provide a data highway over which pictures of the contained area 93 may be projected to another location for remote viewing. In addition, the viewing devices may be equipped with lights for illuminating the contained area 93, such as waterproof electrically powered lights or with light sticks that may be illuminated by chemiluminescence.

Figure 4:
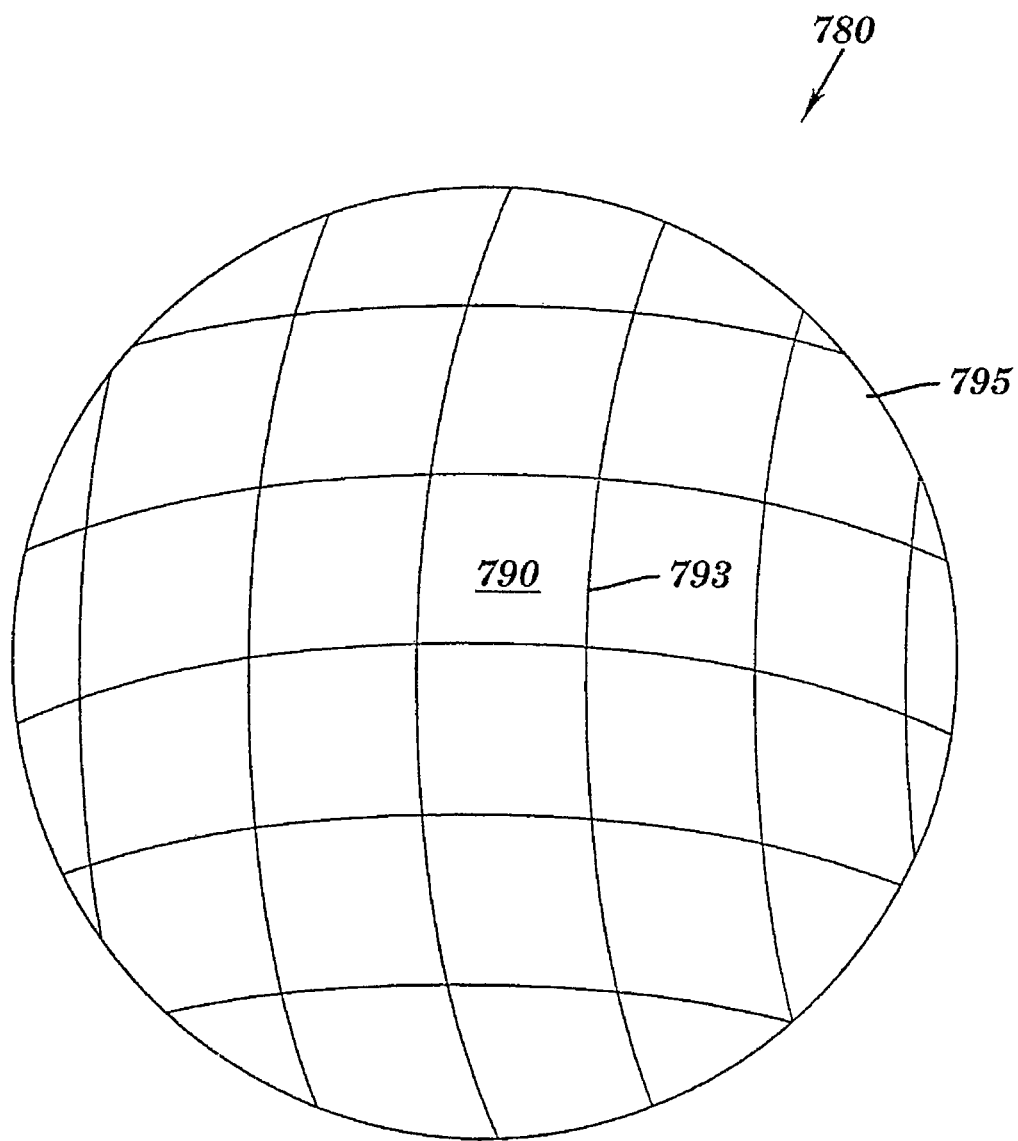
FIG. 4 illustrates a growth packet for improving the environment, according to embodiments of the present invention.

The apparatus 100 may comprise a "closed loop" piping system 45, wherein a portion of the "closed loop" piping system 45 may be defined by paths GA, IM, and LN from vessel 110 via exit lines 145a', 145b' and 145c' respectively, and processing system feed line 60 to a process system 140, such as a filter system, via a valve 51, wherein the process system 140 may include a pump. A remaining portion of the "closed loop" piping system 45 may be defined by paths DH, EJ, and FK to vessel 110 via return lines 147a', 147b', and 147c' respectively, and process system exit lines 62, 149, and 151 via valves 52 and 53. In addition to the filtering system and the pump, the process system 140 may include viewing, monitoring, pressure, and vacuum control, material transport, testing, tooling, and treatment technologies. The treatment technologies may include the aforementioned treatments, for example, removal of toxic chemicals or elements by chemical treatments using additives, reducers, catalysts, microbes, stabilizers, adhesives, charged particles, gases, or elements. The apparatus 100, including the process system 140, may bring a controlled clinical setting out of the laboratory and into the environment. The apparatus 100 also may include isolation valves 50-55, and 69. The growth packet 780, as depicted in FIG. 4 and described in associated text, may be pumped by systems such as the apparatuses 100 or 200 or planting systems 1000, or 3000, depicted in FIGS. 1, 2B, 6A, 9, and 10, infra, used to pump growth packets 900 and 3110 into soil whether above or below waterline as in river bottoms for soil erosion control.

Referring to FIG. 1, when bottom 80 of the body of water 83 may be contaminated with chemicals that may be toxic to animals and humans such as polychlorinated biphenyls (PCBs) or trichloroethylene (TCE) or heavy metals such as Pb, As, Cu, or Hg, the chemical contamination may concentrate in the water and suspended sediment 150 and 152 of the body of water 83, and/or in the precipitated sediment 78 and 78', and/or in the mud 85 and 85', and/or on the bedrock 87 of the bottom 80 of a body of water 83. The sediment 78 and 78' may include silt particles, wherein fine silt has a diameter from about 0.002 mm to about 0.006 mm, medium silt has a diameter from about 0.006 mm to about 0.02 mm, and coarse silt may be from about 0.02 mm to about 0.063 mm. Cleanup processes involving removal of chemical contamination often target removal or cleansing treatment of the sediment 78 and 78', such as silt, because the highest concentration of chemical contaminants may be in the water and suspended sediment 150 and 152 and/or the precipitated sediment 78 and 78' due to a higher surface area of the sediment compared to larger particles of mud 85 and 85'.

A deficiency of commonly used methods of removal of contaminated sediment, such as dredging of contaminated material may be that only a small percentage, sometimes less than 10 percent by weight of the contaminated material, may be actually removed. Commonly used methods of dredging to remove contaminated sediment typically use an open mouthed bucket, such that the water and suspended sediment 150 and 152, the sediment 78 and 78', and the mud 85 and 85' may escape back into the body of water 83 by leaking out of the bucket through the open mouth. Sediment having small diameter such as sediment in the water and suspended sediment 150 and 152, sediment 78 and 78', such as silt, and/or in the mud 85 and 85', that may be light and fluffy by nature, may be hard to contain during commonly used methods of removal of contaminated sediment, such as, for example, dredging operations in the open mouth bucket, for example. A purpose of the present invention may be to overcome at least one deficiency of dredging by providing a container, such as the vessel 110, that may be used to essentially completely contain the contaminated material that may be in the body of water 83, such that when the contaminated materials may be contained in the vessel 110, (and the vessel 210 depicted in FIGS. 2A and 2B and described herein) "the contaminated materials may be essentially quantitatively removed or essentially quantitatively converted to, for example, non-toxic or harmless chemical derivatives.

A second purpose of the present invention may be to overcome the at least one deficiency of dredging by providing a container, such as the vessels 110, (and the vessel 210 depicted in FIGS. 2A and 2B and described herein) that may be used to contain greater than 10% by weight of the contaminated material that may be in the body of water 83, such that when the contaminated materials may be contained in the vessel 110, the contaminated materials may be essentially quantitatively removed or essentially quantitatively converted to, for example, non-toxic or harmless chemical derivatives. Hereinafter, "non-toxic or harmless chemical derivatives" include carbon dioxide, water, and/or hydrogen chloride. Hereinafter, "essentially quantitative removal or essentially quantitative conversion" of the chemical contamination means removal or conversion of essentially 100% by weight of the essentially completely contained contaminated materials. Hereinafter, "contaminated materials" may include portions of the water and suspended sediment 150 and 152, the precipitated sediment 78 and 78', the mud 85 and 85' and the bedrock 87 that have been contaminated with chemicals that may be toxic or harmful to people, wildlife, or vegetation. Alternatively, "contaminated materials" may include portions of the water and suspended sediment 150 and 152, the precipitated sediment 78 and 78', the mud 85 and 85' and the bedrock 87 that have been tainted by other forms of waste such as sewage, sludge or industrial waste that may foul a body of water 83.

Figure 3A:
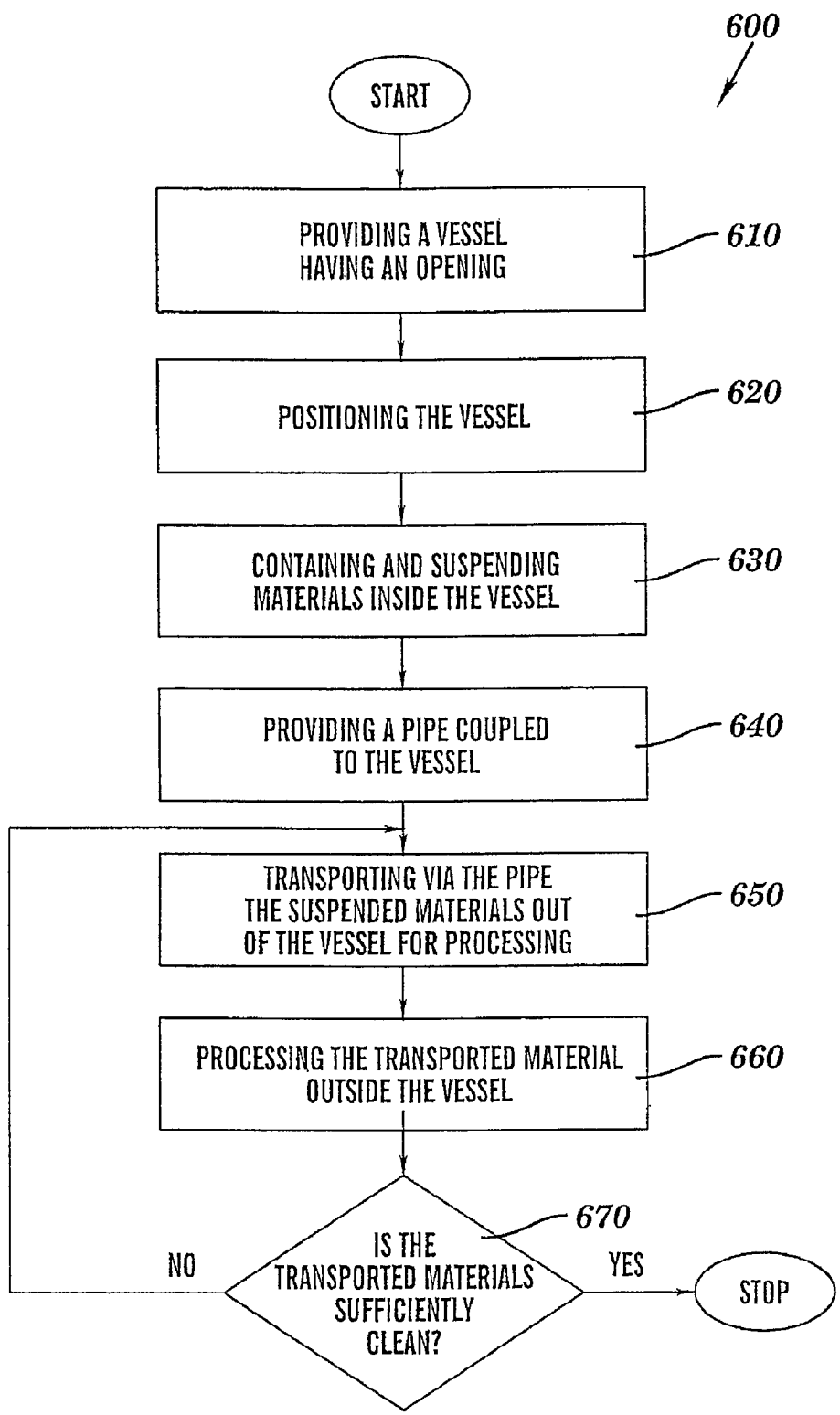
FIG. 3A illustrates a flow chart of a method for operating the apparatus of FIGS. 2A and 2B, according to embodiments of the present invention.

The contaminated material in the bottom 80 of the body of water 83 may be located as to longitude and latitude coordinates in the bottom 80 of the body of water 83, such as in the locations 89 and 91, by testing samples from the locations 89 and 91, using any appropriate testing method for detecting and/or quantifying parts per trillion levels or higher of the chemicals or other form of waste, and mapping the concentrations of the contaminants, such as chemical contaminants, from locations 89 and 91 according to the longitude and latitude coordinates from which the sample(s) originated. Hereinafter, mapping means creating a map showing locations on the surface of the earth, as to longitude and latitude coordinates, that may relate concentrations of the contaminants, such as chemical contaminants, according to the longitude and latitude coordinates (e.g. of locations 89 and 91) from which the samples were taken. The longitudinal and latitudinal coordinates of the locations 89 and 91 may be determined using any appropriate mapping system, such as, for example, a Geographical Positioning System (GPS) 40. If tests show the concentration of the contamination, such as chemical contamination, at a location, e.g. 89 or 91, may be sufficiently high designating the locations as being harmful or toxic to people, wildlife or vegetation, because of sufficiently high contamination, such as chemical contamination, the apparatus 100 may be used to remove the contamination, such as the chemical contamination, as described infra in a method 600 for removing chemical contaminants, as depicted in FIG. 3A. Even 1 part per trillion levels of certain chemical contaminants such as heavy metals, PCB's or dioxins have been found to be sufficiently high to warrant that the chemical contamination may be harmful or toxic to people, wildlife or vegetation.

In the step 620 of the method 600, the apparatus 100 may be positioned over the location designated as having a level harmful to humans, wildlife or vegetation, such as over one or both locations 89 and 91 of the bottom 80 of the body of water 83, as depicted in FIG. 1, resulting in essentially completely containing the contaminated material that may be in the regions 89 and/or 91, such as in contaminated water and suspended sediment 152, and/or in the contaminated precipitated sediment 78, and/or in the contaminated mud 85, and/or in the contaminated bedrock 87, in the vessel 110.

The vessel 110 may be "lowered" into position by mechanical or other means, in accordance with the step 620 of the method 600, as described infra, and depicted in FIG. 3A. By removing air/water/materials out of an interior 93 of the vessel 110, as described in the step 650 of the method 600, a weight of the vessel 110 may drive the edge 82 of the vessel 110 deeper into the bottom 80 of the body of water 83, resulting in creating a releasable seal 95 at the edge 82 of the vessel 110, that may be formed from sediment 78' and mud 85' of the bottom 80 outside of the vessel 110 pressing against the edge 82 and either sediment 78, mud 85 or the bedrock 87, depending on how deep the vessel 110 was driven. The releasable seal 95 thereby may isolate the interior 93 from the water 150, and/or the bottom 80 of the body of water 83, that may be outside the vessel 110.

In the positioning step 620 of the method 600, the vessel 110 may be partially submerged or completely submerged below the surface 170 of the body of water 83, as long as the edge 82 directly and physically contacts the bottom 80 of the body of water 83.

In the containing and suspending step 630 of the method 600, paddles 125a and 125b, such as augers, spray heads, whips, props, fluid and gas distribution devices, etc. may provide agitation of the interior 93 of the vessel 110, resulting in suspending a portion or essentially all of the bottom material, e.g., 78, or 85 of the bottom 80 that may be contained in the interior 93 of the vessel 110, wherein the suspended portion may include the contaminated material. The contaminated material may be a range from 0-100 percent by weight of the total material of the bottom 80 in the interior 93 of the vessel 110.

In the step 630, a rate of agitation necessary to suspend the contaminated material, for example, in locations 89 and 91 may be empirically determined, based on the weight percent of the bottom material targeted for removal, wherein higher agitation may be needed to suspend more of the portion of the bottom 80 having contaminated material. The contaminated suspended material in the water and suspended material 152 may be conveyed through the "closed loop" piping system 45 to a processing system 140 such as a filter system having in-line chemical testing equipment in order to identify the suspended materials that may be contaminated and to separate them from a fluid such as water in the suspended material and water 152. In one embodiment, the identified suspended material that may be contaminated can be conveyed from the interior 93 of the vessel 110 through the exit lines 145a', 145b' and 145c', through the processing system feed line 60, through the valve 51 to the processing system 140 where the contaminated suspended materials may be removed. The separated fluid can be recycled back into the vessel 110 through the valve 53, the process system exit lines 62 and 149, the valve 52, the process system exit line 51, the return lines 147a', 147b', and 147c', and finally back to the interior 93 of the vessel 110. A rate of removal of contaminated materials such as, e.g., contaminated soil and silt, from the vessel 110 and rate of return of the processed fluids and processed contaminated material, such as, e.g., soil and silt, to the vessel 110 may be controlled such that an essentially net zero pressure difference may be measured between the interior 93 and the outside of the vessel 110, e.g. at the open rim 90 of the vessel 110, and at the releasable seal 95 that may be formed from bottom 80, e.g., sediment 78' and mud 85' of the bottom 80, outside of the vessel 110 that may releasably seal the edge 82 onto either sediment 78, mud 85 or the bedrock 87, depending how deep the vessel 110 was driven. Therefore, in the steps 650-660, essentially no contaminated suspended material may escape from the essentially complete containment provided by the apparatus 100 during operation of the "closed loop" piping system 45 as described in the steps 610-670 of the method 600, as described infra and depicted in FIG. 3A. "Additives" or "reducers" (catalysts, microbes, stabilizers, adhesives, charged particles, gases, elements, known or unknown) can be fed from feed line 143 into the "closed loop" piping system 45 through valve 50.

An efficiency of the processing system 140 may be determined by comparing a turbidity of the fluid in the return lines 147a', 147b', and 147c' to the turbidity of the fluid and suspended soil and silt in the exit lines 145a', 145b' and 145c'. It has been found that the percent efficiency of removal of contaminated material by filtering may be essentially 100.0% if the processing system 140 may include 0.2 to 100 micron paper or cloth filters, wherein the percent efficiency may be determined by converting a ratio of the turbidity of the fluid into the processing system 140 and the turbidity of the fluid out of the processing system 140 to percent. Efficiency between 50% and 95% may be achieved using sand filters such as for filtering swimming pools, having #20 silica with a particle diameter of the sand being from about 0.40 mm to about 0.50 mm, available from Jandy, PO Box 6000, Petaluma, Calif. 94955-6000. Recommended sands may be sand grade 0.45 mm to about 0.55, having an average diameter of 0.46 mm, available from Wedron/Best Sand Company, or sand grade 0.45 mm to about 0.55 mm, having an average diameter of 0.48 mm, available from U.S. Silica/Silurian Filter Sand. Weight of sand for charging the filter may be determined by one skilled in the art with a minimum of experimentation based on choosing a weight of sand appropriate to filter 2.0 to 2.5 times the volume of suspended sediment and water in the vessel 110 per hour, without exceeding 50 psi internal pressure in the sand filter. The processing system 140 can be a micro-filtration system or a chemical reaction process that may be activated by light such as lasers, light emitting diodes including laser emitting diodes, UV or thermal energy. Once monitoring levels are met, recycled materials, such as the treated contaminated materials or growth packets 780 and 900, as depicted in FIGS. 1, 2B, 4 and 5, infra, may be returned into the vessel 110, through the closed-loop piping system 45, enabling the materials to settle out, resulting in refilling the extraction site with soil or silt, wherein the chemical contamination has been sufficiently removed such that the soil or silt meets monitoring levels and wherein erosion of the river bottom 80 of the body of water 83 may be minimized because the returned recycled materials, such as filtered or processed soil or silt re-fills any holes left when the vessel 110 may be withdrawn for relocation to another contaminated location of the river bottom.

The vessel 110 allows for removals "in place" with continuous monitoring and minimal exposure to the surroundings. This process 140 exists for extraction without released re-suspension.

In one embodiment, the present invention solves the problem of containing the contaminated material by providing a resealable/sealable vessel 110 for sampling, viewing, monitoring, separating, testing, treating, injecting, replacing or removing contaminated materials that include silt, sludge, stone materials, ores, metals, or elements, etc. from a bottom 80 of a body of water 83.

Generally, the present invention may be an apparatus 100 for sampling, viewing monitoring, separating, testing, treating, injecting, replacing or removing materials that include silt, sludge, stone materials, ores, metals, or elements, etc. from a bottom of a body of fluids, such as, for example, a chemically contaminated bottom 80 of a body of water 83. The apparatus 100 may comprise an open-faced vessel 110, a global positioning device 40, and a closed loop piping system 45.

Figure 2A:
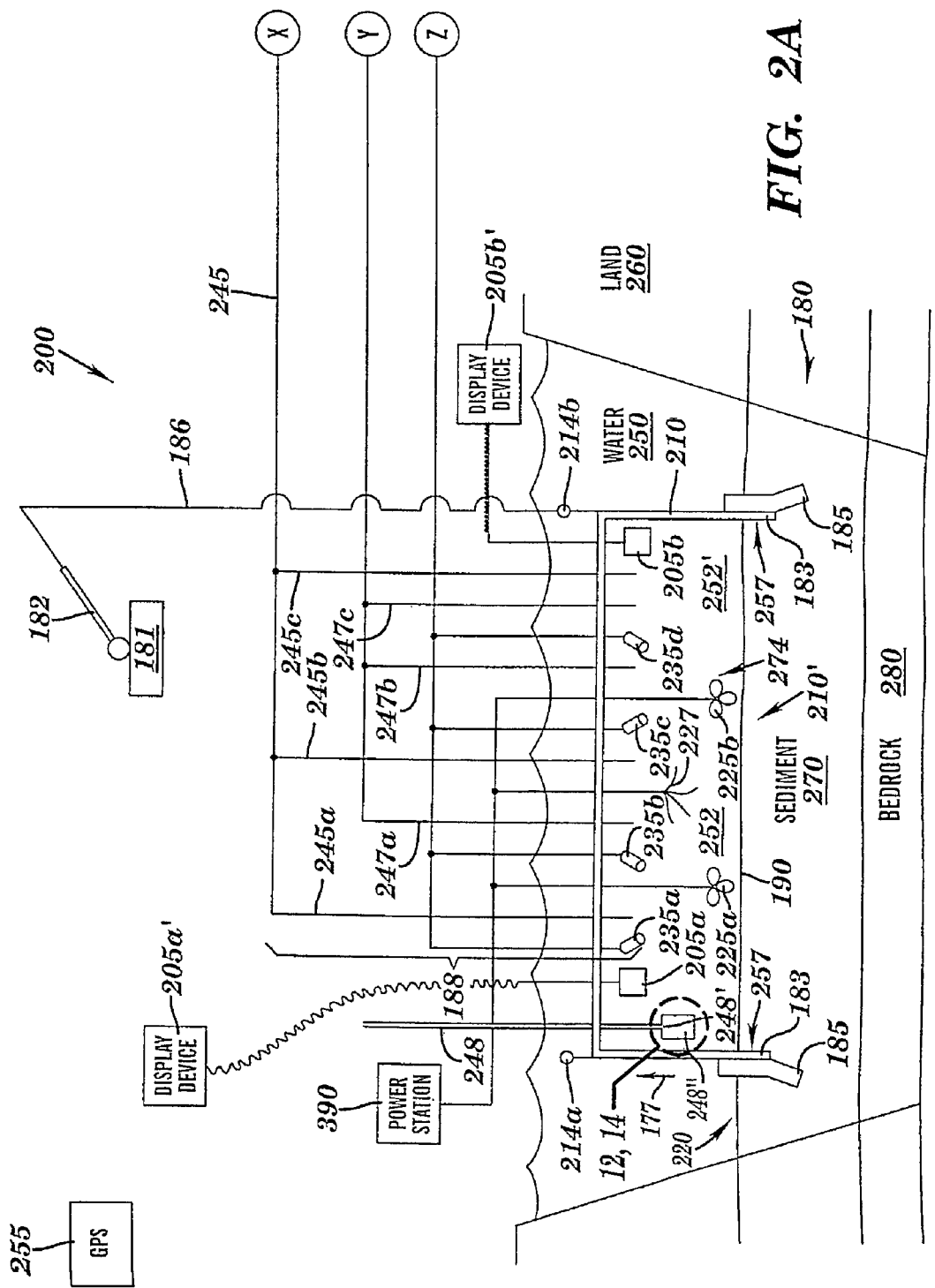
FIGS. 2A and 2B illustrate an apparatus for removing and treating materials in a body of water, according to embodiments of the present invention.
Figure 2B:
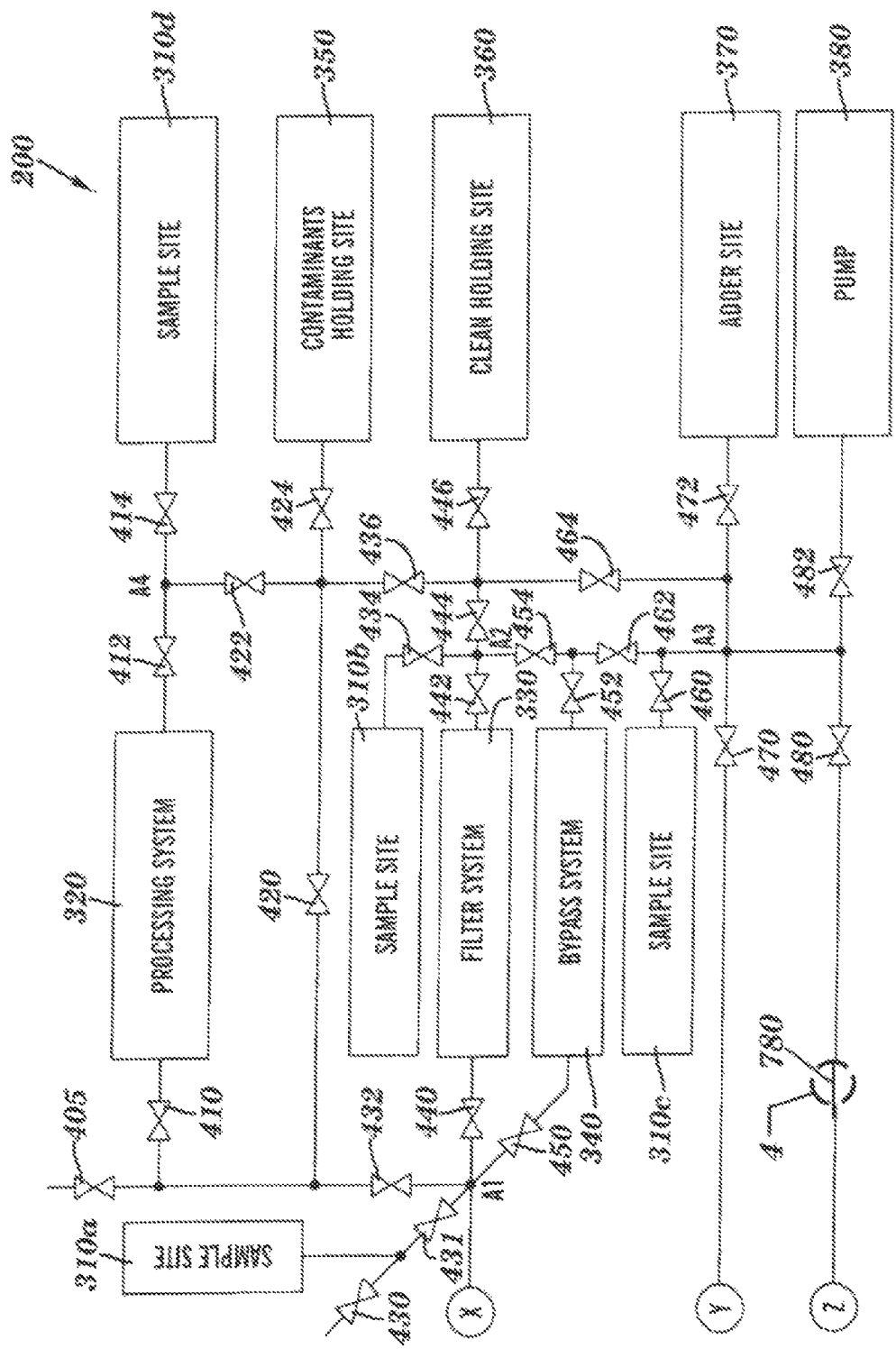

The open faced vessel 110 may form a releasable seal 95 with the bottom 80 of the body of water 83 and may include at least one agitator 125a, 125b, 135a, 135b, 135c, 135d, and 127 for suspending portions of contaminated materials from the bottoms such as, for example, silt, sludge, stone materials, ores, metals, or elements, etc. Power station 120 may provide power, such as, for example, mechanical or electrical power. The at least one agitator 125a, 125b, 135a, 135b, 135c, 135d, and 127 may also may include at least one outlet port 145a, 145b, and 145c through which a mixture of the portions of the bottoms and water may be withdrawn from the vessel 110 for monitoring, separating, testing, treating, injecting, replacing, or removing the portions. The agitators may be variable speed impellers 125a and 125b, whip 127 or nozzles 135a, 135b, 135c, 135d for directing a stream of water or air at variable pressures from any appropriate device, such as, air or water jets 130. The stream of water or air at variable pressure may be conveyed through transfer line 153, branching through lines 65, 66, 67, and 68 into nozzles 135a, 135b, 135c, and 135d, respectively. The area sampled may be any area equivalent to the area of contamination, such as, e.g., chemical contamination, limited only by practical considerations such as costs of materials and benefit from minimizing the number of relocations of the vessel 110 in order to sample the contaminated area. In one embodiment the vessel 110 or 210 (as depicted in FIGS. 2A and 2B, and described herein) may be from about 1-1,000,000 sq. ft. to sample the area of contamination. The vessel 110, impellers 125a and 125b, whips 127 or nozzles 135a, 135b, 135c, 135d may be metal, or metal alloy, such as, for example, carbon steel, aluminum, stainless steel, rubber, plastic or composites.

The global positioning device (GPD) 40 or other appropriate computerized positioning device may be for determining a position of the vessel to within +/−0.12 inches of, for example, a known chemically contaminated site on the bottom 80 of the body of water 83.

The process system 140 may include a two directional pump for circulating materials into and out of the vessel 110. It may be possible for a vacuum or negative pressure to result in the vessel 110 if the closed loop piping system 45 may be under a vacuum when the contaminated materials, such as, for example, the water and suspended sediment, 152, silt, 78, or mud, 85 inside the vessel 110 may be removed from the vessel 110 and drawn into the piping system 45, wherein the releasable seal 95 may prevent relief of the vacuum, such as, by leakage of materials, such as, for example, uncontaminated silt, 78', uncontaminated mud, 85' or uncontaminated water 150 into the vessel 110. Alternatively, it may be possible for a positive pressure to result in the vessel 110 if the closed loop piping system 45 may be full of air or any other compressible fluid when the contaminated materials, such as, for example, the water and suspended sediment, 152, silt, 78, or mud, 85 inside the vessel 110 may be removed from the vessel 110 and drawn into the piping system 45, wherein the releasable seal 95 may prevent relief of the pressure buildup by leakage of materials, such as, for example, the water and suspended sediment, 152, silt, 78, or mud, 85 out of the vessel 110. A portion of the contaminated materials, such as, for example, sediment, 78, such as silt, that may be higher in chemical contamination, may be removed from the water by the processing system 140, such as, e.g., micro-filters, and water and remaining portions of the material, such as, for example, mud, 85, may be returned to the vessel 110. The processing system 140, such as, e.g., the micro-filters may be cleaned to remove chemically contaminated materials, such as, e.g., silt or other micro-materials, with high frequency bursts of pressure or by ultra sonic bursts during periods when the "closed loop" apparatus 100 may be inactive. The monitoring may include testing for chemicals or elements, known, or unknown, such as polychlorinated biphenyls (PCB), dioxin, and other toxic chemical solvents such as trichloroethylene (TCE). The treatment may include, for example, removal of toxic chemicals or elements by, for example, chemical treatments using additives, reducers, catalysts, microbes, stabilizers, adhesives, charged particles, gases, or elements. Once treated, cleaned, separated materials, such as the portions absent the silt, may be returned to the bottom 80 of the body of water 83 via the closed loop piping system 45.

In summary, the claimed invention may allow for removals "in place" with continuous monitoring and minimal exposure to the surroundings. The claimed process may extract toxic chemicals from portions of the bottom 80 or may remove silt and/or may return remaining portions of the bottoms in areas as small as 1 square feet with exact positioning within +/−0.12 inches of, for example, a known chemically contaminated site on the bottom of the body of water 83. FIGS. 2A and 2B illustrate an apparatus 200, such as an Open or Closed Loop Extraction Lunch Box, OCLELB, comprising at least one "open or closed loop" piping system(s) 188, according to embodiments of the present invention. The apparatus 200 may comprise, illustratively, a vessel 210, at least one pipe(s) 245a, 245b, 245c, 247a, 247b, 247c, and 248, at least one agitating device(s) 235a, 235b, 235c, 235d, 225a, 225b, and 227, at least one observing device(s) 205a, 205a' and 205b, 205b', at least one sample site(s) 310a, 310b, 310c, and 310d, at least one processing system(s) 320, and/or a filter system 330, and/or a by-pass system 340, and/or a contaminants holding site 350, and/or a clean holding site 360, and/or an adder site 370, and/or a pump 380, and/or a power station 390, and/or at least one isolation valve(s) 405-482. The growth packet 780, as depicted in FIG. 4 and described in associated text, may be pumped by systems such as the apparatuses 100 or 200 or planting systems 1000, or 3000, depicted in FIGS. 1, 2B, 6A, 9, and 10, infra, used to pump growth packets 900 and 3110 into soil whether above or below waterline as in river bottoms for soil erosion control.

The vessel 210 may comprise an opening 210' adapted for facing and being in direct physical contact with the bottom 180 of a body of water 250 so as to form a contained area 274 inside the vessel 210. The body of water 220 may include water and suspended sediment 250 and bottom 180 of the body of water 220, wherein the bottom 180 of the body of water 220 includes sediment 270 and bedrock 280. The vessel 210 may be made of rigid material such as plastic, rubber or metal. Alternatively, the vessel 210 may be made of flexible material such as flexible rubber. The vessel 210 may have any appropriate solid geometric shape such as polygon, cubic, cylindrical, spherical, pyramidal, rhomboid or conical. The vessel 210 can be made of steel, plastic, or any material that can isolate and contain air and liquids. In one embodiment, a flexible skirt 185 may extend a rim 183 of the vessel 210, to provide a flexible extension of the rim 183, wherein the flexible skirt 185 may wrap around rocks or other solid debris on the bottom 180 of the body of water 250, enabling the flexible skirt 185 of the vessel 210 to be in direct physical contact with the bottom 180 so as to isolate the contained area 274 of the vessel 210 from the outside of the vessel, even though the rim 183 may be prevented from physically contacting the bottom 180 because it may not be able to penetrate the rock or debris.

In one embodiment, the vessel 210 may comprise one or more hooks 214a and 214b. Illustratively, the hook 214b can be used for coupling via cable 186 with a lifting device 182 such as a crane, wherein the lifting device 182 may be secured to a floating vessel 181 such as a boat or barge.

The vessel 210 can have any shape that facilitates its movement (lifting and lowering) in or out of the water or to enable it to circumvent rocks or debris on the bottom 180 of the body of water 250.

Figure 6A:
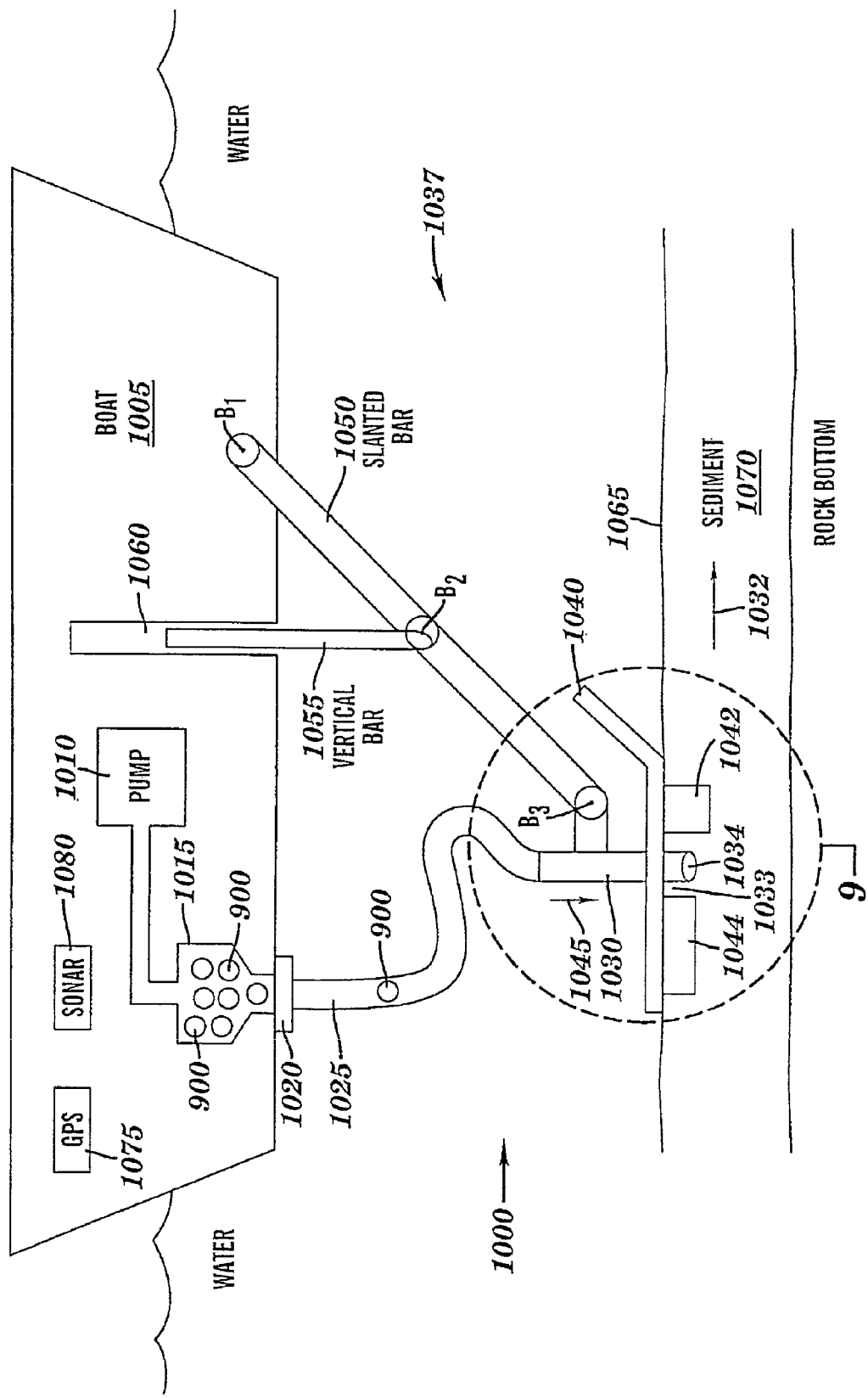
FIG. 6A illustrates a planting system that can be used for planting the growth packets of FIGS. 4 and 5, according to embodiments of the present invention.
Figure 9:
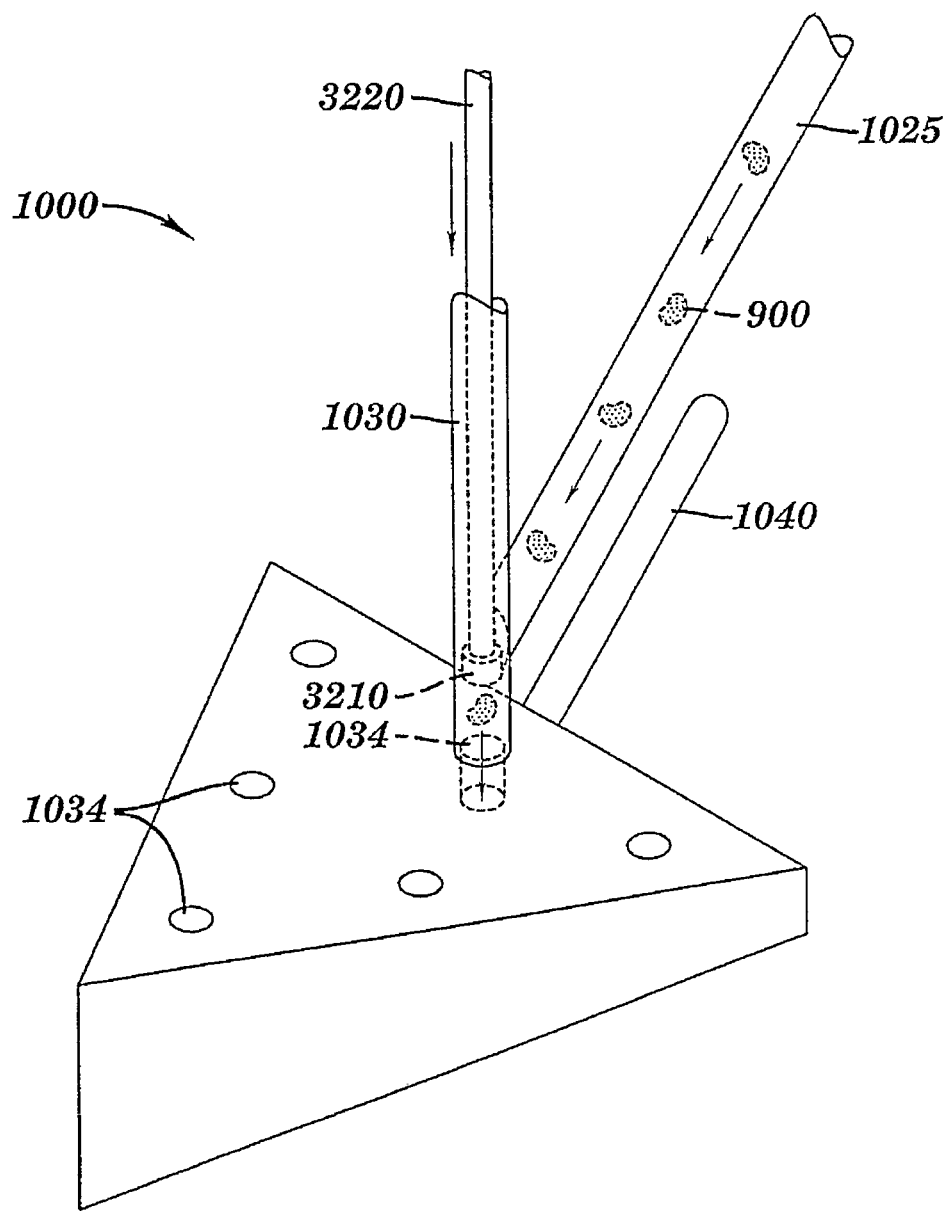
FIG. 9 illustrates an exploded side elevation view of the planting sled, according to embodiments of the present invention.
Figure 10:
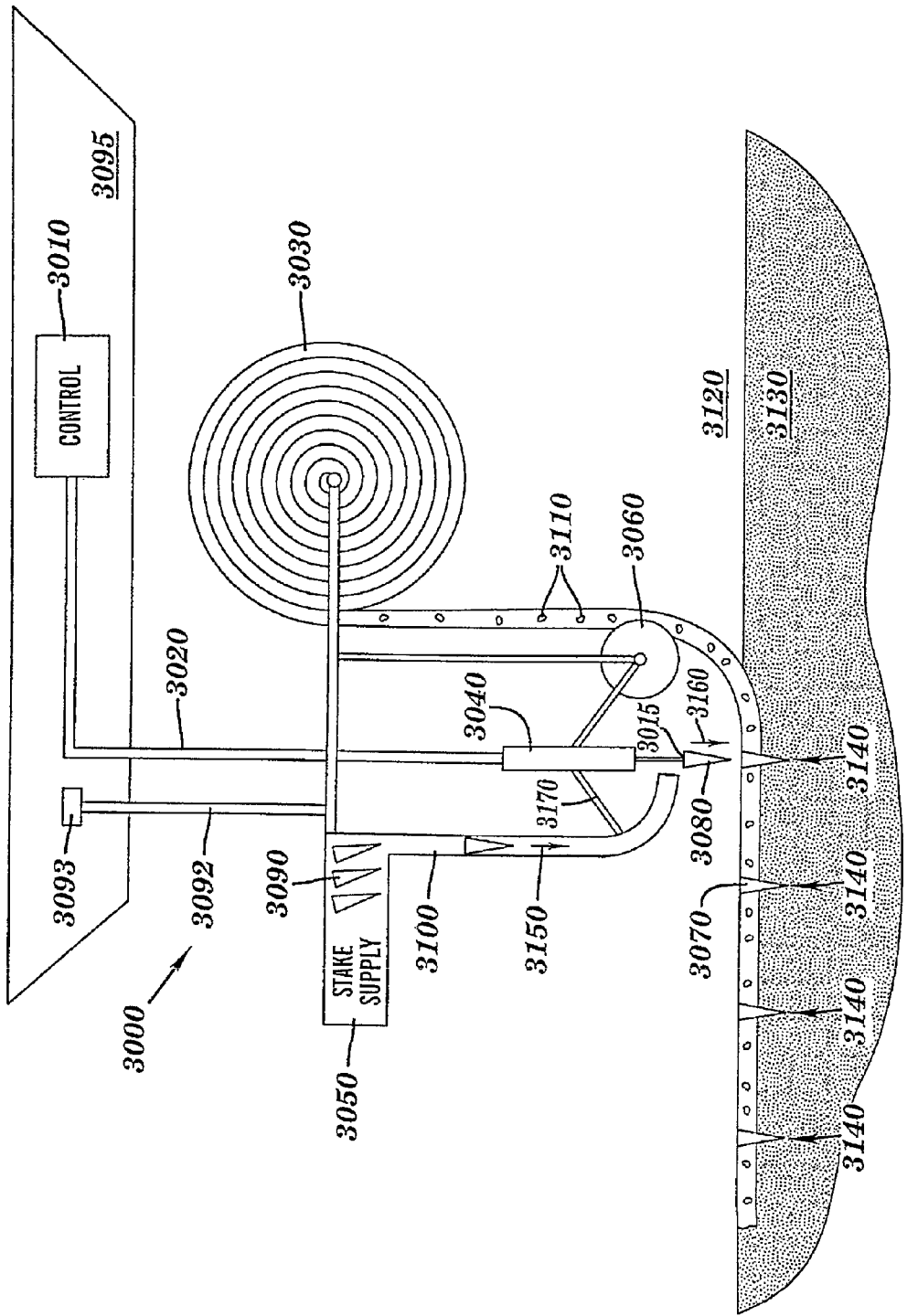
FIG. 10 illustrates a Blanket Roll Planting System (BR Planting System), according to embodiments of the present invention.

In one embodiment, the at least one pipe(s) 248 can comprise an attachment 248", wherein the attachment 248" may be operatively coupled to the pipe 248 at an opening 248' of the at least one pipe(s) 248. The attachment 248" may be a drill head or auger to facilitate inserting the at least one pipe(s) 248 into the bottom 180 of the body of water 220. The attachment 248" of the at least one pipe(s) 248, when the attachment 248" may be a drill head or auger, can be used for performing core sampling, wherein a core sample is a sample of soil or sediment from the bottom 180 of the body of water 220, as depicted in FIG. 2A. In one embodiment, with the help of the attachment 248", such as, for example, the drill head or auger, the at least one pipe(s) 248 may be inserted into the bottom of the body of water 220 such that a column of the bottom materials (i.e., a core sample) may be inserted into the interior of the at least one pipe(s) 248. The attachment 248", such as the drill head or auger, may be mounted on a drill head or auger sled for easy positioning, such as the planting sled 1040 of the apparatus 1000 as depicted in FIGS. 6A and 9 and described herein, wherein the attachment 248", such as the drill head or auger may be substituted for the ram piston 3220, as depicted in FIG. 10, infra. Then, the core sample can be transported via the at least one pipe(s) 248 out of the interior 274 of the vessel 210 for testing.

Figure 12:
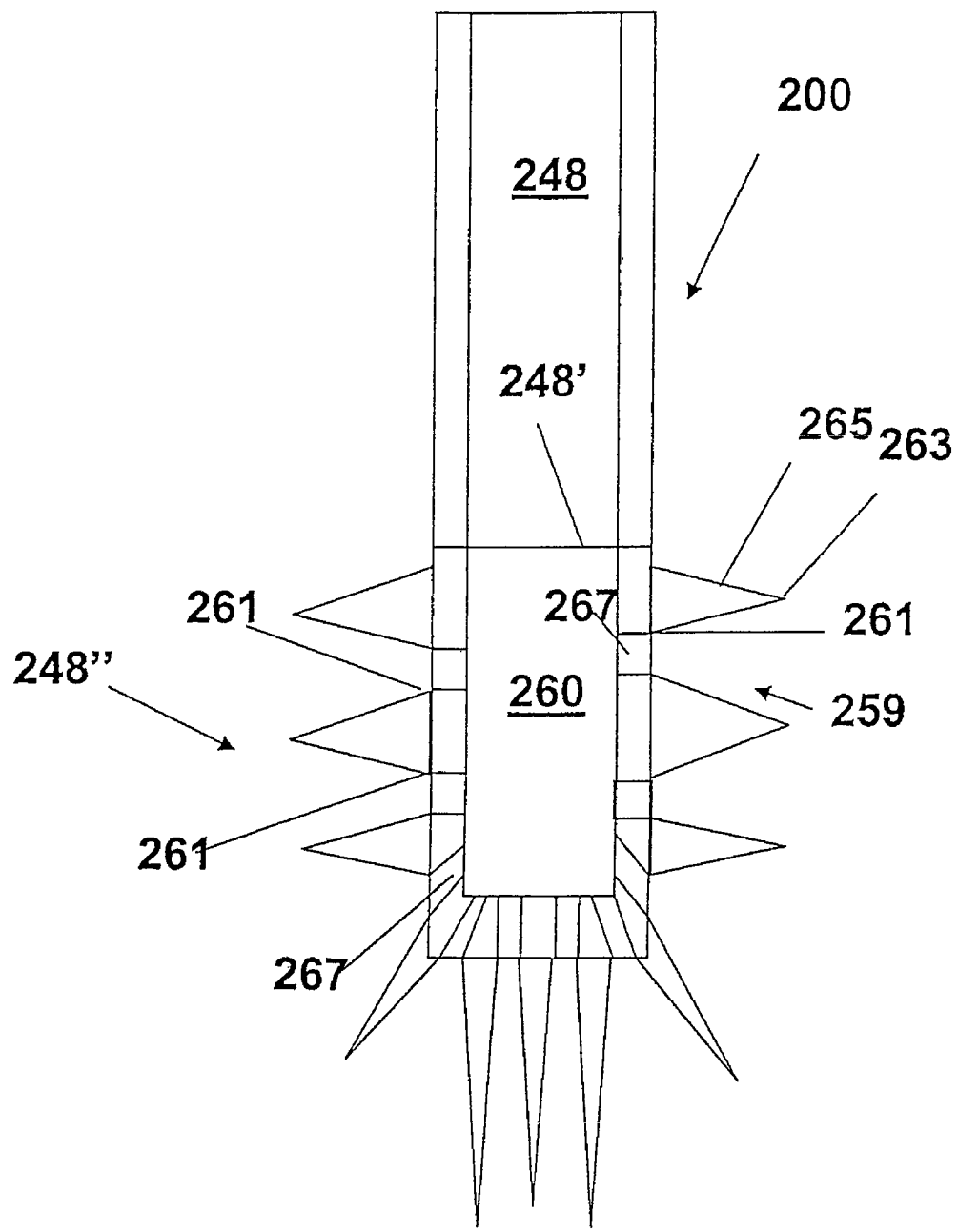
FIG. 12 depicts a longitudinal cross sectional view of the apparatus, illustrating an exploded view of an attachment, as depicted in FIG. 2A, supra, according to embodiments of the present invention.

Alternatively the attachment 248" may be a filter. FIG. 12, infra, depicts a transverse cross section of the attachment 248", when the attachment 248" may be a filter.

Referring to FIGS. 2A and 2B, each of the at least one agitating device(s) 235a, 235b, 235c, and 235d can be in the form of a nozzle through which a fluid (usually water) may be pumped under high pressure into the interior 274 of the vessel 210 so as to agitate the materials inside the vessel 210. Each of the at least one agitating device(s) 225a and 225b can be an impeller having multiple blades. The at least one agitating devices 225a and 225b can be powered by a power station 390.

The at least one agitating device(s) 227 can have the form of a whip having multiple branches. Each branch may have a hollow core through which water (or other fluids) can be pumped under high pressure into the interior 274 of the vessel 210 so as to agitate the materials inside the vessel 210. The whip 227 can spin or rotate while water may be being pumped through it into the interior 274 of the vessel 210. Similar to the at least one device(s) 225a and 225b, the at least one agitating device(s) 227 can also be powered by the power station 390.

In one embodiment, the at least one observing device(s) 205a, 205a' can comprise a sonar head 205a and a sonar display 205a'. The sonar head 205a can be used for collecting information about the thickness of the sediment layer 270. The sonar display 205a' can be used for displaying the information collected by the sonar head 205a.

In one embodiment, the at least one observing device(s) 205b, 205b' can comprise a camera 205b and a display 205a'. The camera 205b can be used for collecting image data inside the vessel 210. The display 205a' can be used for displaying the image data collected by the camera 205b. The camera 205b can include a light bulb (not shown) that can emit light sufficiently strong for viewing the entire interior 274 of the vessel 210. In one embodiment, the at least one observing device(s) 205b, 205b' can be used as a camera for determining if the vessel 210 may be lowered upon an uneven bottom 180 of the body of water 220, such as a river bottom or upon a rock or debris at the river bottom. If so, the position of the vessel 210 can be adjusted such that the edge of the vessel 210 would touch the river bottom so as to isolate the interior 274 of the vessel 210 from the outside of the vessel 210.

FIG. 3A illustrates a flow chart of a method 600 for transporting materials from a bottom of a body of water for processing, the method comprising (a) providing a vessel including an opening, (b) positioning the vessel such that the opening may be facing the bottom of the body of water and may be in direct physical contact with the bottom of the body of water, (c) containing and suspending the materials inside the vessel, (d) providing a first pipe coupled to the vessel, and (e) transporting, via the first pipe, the suspended materials from an interior of the vessel to an exterior of the vessel. The method 600 can be used for operating the apparatus 200 of FIGS. 2A and 2B, according to embodiments of the present invention. With reference to FIGS. 2A, 2B, and 3A, the method 600 starts at step 610 in which a vessel 210 having an opening 210' may be provided. Then, in step 620, the vessel 210 may be positioned at the bottom 180 of the body of water 220 such as the bottom of a river (or any other body of water).

In one embodiment, the vessel 210 may be positioned, wherein the opening 210' may face a location 190 of contaminated material such as, for example, chemically contaminated material. The location 190 may have been positioned on a map as to its longitude and latitude coordinates using aforementioned chemical mapping techniques, such that an operator of the apparatus 200 may be able to position the apparatus 200 over the location 190 of contaminated material, as depicted in FIG. 2A. In one embodiment, the operator of the apparatus 200 may lower the apparatus 200 by a crane 182 using the hooks 214a and 214b to the location 190 of a first untreated position at the bottom 180 of the body of water 220 such that the opening 210' may be facing the bottom 180. In one embodiment, the location 190 of the first untreated position may be located using a GPS device 255. In one embodiment, the pump 380 may pull materials including air, water, bottom material such as sediment and/or mud from the interior 274 of the vessel 210 via the at least one pipe(s) 245a, 245b, and 245c, resulting in drawing a rim 183 into the bottom 180 of the body of water 220, such as the river bottom, such that the rim 183 may have physically and directly contacted the bottom 180 of the body of water 220, resulting in forming a releasable seal 257 with the bottom 180 of the body of water 220, such as a river bottom. In some embodiments, no air/water may remain inside the vessel 210. The pump 380 can continue to pull air/water out of the vessel 210 so as to further decrease the pressure inside the vessel 210. As a result, the vessel 210 may be releasably sealed into the bottom 180 of the body of water 220, such as the sediment layer 270 above the bedrock 280. In general, the pump 380 can be used for moving suspended materials 252' throughout the apparatus 200, resulting in removal or chemical conversion of the contaminated material from the bottom 180 of the body of water 220. As a result, materials may flow from the interior 274 of the vessel 210 out of the vessel 210. Also, pumping materials into the interior 274 of the vessel 210 after completing methods 600 or 700 may release the releasable seal 257, allowing the vessel 210 to release from the bottom 180 of the body of water 220, such as the river bottom. The pump 380 can also be used for pumping materials (mostly water) out of the vessel 210 so as to decrease the pressure inside the vessel 210. As a result, materials will flow into the interior 274 of the vessel 210 from the at least one pipe(s) 147a, b, c. Also, pumping materials out of the vessel 210 may increase a strength of the releasable seal 257 between the vessel 210 and the bottom 180 of the body of water 220, such as the river bottom.

In one embodiment, the vessel 210 may be designed to be airtight on all sides except the opening 210'. As a result, when the vessel 210 has been inserted in the bottom 180 of the body of water 220, such as the sediment layer 270 at the bottom of the river, the materials inside the vessel 210 (i.e., in the interior 274) may be essentially completely isolated from an exterior of the vessel 210.

Next, in step 630, materials inside the vessel 210 may be essentially completely contained and suspended inside the vessel 210. In the containing and suspending step 630 of the method 600, paddles 225a and 225b, such as augers, spray heads, whips, props, fluid and gas distribution devices, etc. may provide agitation of the interior 252 of 252 of the vessel 210, resulting in suspending a portion or essentially all of the bottom material, e.g., 270, or 280 of the body of water 220 that may be contained in the interior of the vessel 210, wherein the suspended portion may include the contaminated material. In one embodiment, the at least one agitating device(s) 235a, 235b, 235c, 235d, 225a, 225b, and 227 may be operated to suspend the contaminated material in the mixture 252' in the interior 252 of the vessel 210. As a result, the contaminated materials in the bottom 180 of the body of water 220, such as, e.g., the contaminated materials in the sediment layer 270 may form a mixture 252' by removing contaminated materials from the sediment layer 270 and interspersing the contaminated materials with water in the interior 252 of the vessel 210. As long as agitation continues, the contaminated materials such as, e.g., the contaminated sediment in the mixture 252' do not precipitate to the bottom. In other words, the contaminated sediment materials in the mixture 252' may be said to be suspended in the mixture 252'. In step 630, the mixture 252' that may contain contaminated sediment materials may be essentially completely contained and suspended in the mixture 252' in the interior 252 of the vessel 210.

Then, in step 640, an at least one pipe(s) 245 may be provided which may be coupled to the vessel 210. In one embodiment, the at least one pipe(s) 245 may branch as at least one branch pipe(s) 245a, 245b, and 245c. Then, in step 650, the materials suspended inside the vessel 210 may be transported out of the vessel 210 through the pipe 245 for processing. More specifically, the mixture 252' containing the removed and suspended contaminated sediment materials may be transported out of the vessel 210 via the pipe 245 for processing.

Each of the at least one isolation valve(s) 405-482 can be either open or closed. If open, the at least one isolation valve(s) 405-482 may allow fluid to pass through. When closed, the valve(s) prevents fluid from passing through. The valves 405-482 in the apparatus 200 can be used for isolating different portions of the apparatus 200. By opening some of the valves 405-482 and closing the remaining valves, materials can be carried around the apparatus 200 along a desired path for processing. In one embodiment, in order to keep the pressure inside the vessel 210 unchanged, materials (e.g., air or water) may be allowed to flow from the clean holding site 360 to the interior 274 of the vessel 210 via the at least one valve(s) 446, 464, and 470, and the at least one pipe(s) 247a, 247b, and 247c. The clean holding site 360 can be used for holding a filtrate transported from the interior 274 of the vessel 210 via the filtering system 330. The materials in the clean holding site 360 can undergo further processing and treatment before being either transported back into the interior 274 of the vessel 210 or shipped elsewhere. The adder site 370 can be used for holding materials to be added to the interior 274 of the vessel 210. In one embodiment, each of the at least one valve(s) 446, 464, and 470 may be configured to become open when the pressure difference between its two ends exceeds some pre-specified value. As a result, when the mixture 252' containing the removed sediment materials may be pumped out of the vessel 210 via the pipe 245, the at least one valve(s) 446, 464, and 470 may automatically open to allow materials (e.g., air and/or water and/or treatment chemicals to convert toxic or harmful contaminants into carbon dioxide, water or HCl) to flow from the clean holding site 360 to the interior 274 of the vessel 210. Therefore, the pressure inside the vessel 210 may remain unchanged.

Then, in step 660, the materials transported out of the vessel 210 may be processed outside the vessel 210. In one embodiment, the mixture 252' containing the removed contaminated sediment can be transported from inside the vessel 210 to the processing system 320 via the at least one pipe(s) 245a, 245b, and 245c (i.e., the branches off pipe 245) and the at least one valves 432 and 410. In the processing system 320, the mixture 252' can undergo thermal, chemical, radiation, or other processes so as to treat (remove, alter, etc.) the contaminants from the mixture 252' so they become less or nontoxic. After processing, the mixture 252' can be transported either back to the interior 274 of the vessel 210 via the at least one valve(s) 412, 422, 436, 464, and 470 and the at least one pipe(s) 247a, 247b, and 247c or to the clean holding site 360 via the at least one valve(s) 412, 422, 436, and 446. The materials in the clean holding site 360 can be returned to the interior 274 of the vessel 210 via the at least one valve(s) 446, 464, and 470, and the at least one pipe(s) 247a, 247b, and 247c.

In one embodiment, the mixture 252' can be transported to the filtering system 330 via the at least one valve(s) 440 so that contaminants in the mixture 252' can be filtered out. The filtered contaminants can be periodically removed from the filter system 330. The remaining mixture after filtering can be transported either back to the interior 274 of the vessel 210 via the at least one valve(s) 442, 454, 462, and 470 and the at least one pipe(s) 247a, 247b, and 247c or to the clean holding site 360 via the at least one valve(s) 442, 444, and 446. The materials in the clean holding site 360 can be returned to the interior 274 of the vessel 210 via the at least one valve(s) 446, 464, and 470, and the at least one pipe(s) 247a, 247b, and 247c.

In one embodiment, the mixture 252' containing the removed sediment materials can be transported from inside the vessel 210 to the contaminants holding site 350 via the at least one pipe(s) 245a, 245b, and 245c, the valve 450, the by-pass system 340, and the at least one valve(s) 452, 454, 444, 436, and 424. In the contaminants holding site 350, the mixture may undergo processes similar to those in the processing system 320 described above. After being processed at the contaminants holding site 350, the mixture can be transported either back to the interior 274 of the vessel 210 via the at least one valve(s) 424, 436, 464, and 470 and the at least one pipe(s) 247a, 247b, and 247c or to the clean holding site 360 via the at least one valve(s) 424, 436, and 446. The materials in the clean holding site 360 can be returned to the interior 274 of the vessel 210 via the at least one valve(s) 446, 464, and 470 and the at least one pipe(s) 247a, 247b, and 247c.

The concentration of contaminants may be monitored along the at least one path(s) by locating an at least one sample site(s) 310a, 310b, 310c, and 310d on the at least one path(s) of the mixture 252' from the vessel 210 before and after processing.

More specifically, the sample site 310a may be directly coupled via the valve 431 to a node A1 which the mixture 252' from the inside of the vessel 210 flows through before going to different destinations. Here, "directly coupled" means that there may be no processing in between. As a result, samples of the mixture 252' before processing can be taken via the valve 431 from the sample site 310a, such that the concentration of the contaminants in the mixture 252' before processing can be measured. In one embodiment, in the step 670 of the method 600, when the measured concentration of the contaminants may be below a pre-specified level, the processing may be stopped and either (i) the vessel 210 may be lifted from the current location and lowered and inserted into another location on the bottom of the body of water 220 or (ii) more sediment materials from the top of the sediment layer 270 may be removed by agitation as described above for further processing. In one embodiment, the pre-specified level of contaminants can be specified by the owner(s) of the body of water 250 (FIG. 2A) or authorities responsible for cleaning the sediment 270 (FIG. 2A).

Similarly, the sample site 310b may be directly coupled via the valve 434 to a node A2 which the mixture 252' from the filtering system 330 exits through before going to different destinations. As a result, samples of the mixture 252' after filtering can be taken via the valve 434 to the sample site 310b where the concentration of the contaminants in the mixture after filtering can be measured so that the quality of the filtering process can be monitored.

Similarly, the sample site 310c may be directly coupled via the valve 460 to a node A3 which the mixture 252' after processing flows through before returning to the interior 274 of the vessel 210 via the at least one pipe(s) 247a, 247b, and 247c. As a result, the sample site 310c can be used for monitoring a concentration of contaminants in the mixture 252' that flows back to the interior 274 of the vessel 210, after processing.

Similarly, the sample site 310d may be directly coupled via the valve 414 to a node A4 which the mixture 252' from the processing system 320 exits through before going to different destinations. As a result, samples of the mixture 252' after processing can be taken via the valve 414 to the sample site 310d where the concentration of the contaminants in the mixture after processing can be measured so that the quality of the processes performed in the processing system 320 can be monitored.

In step 670, a determination may be made as to whether the materials transported out of the vessel 210 may be sufficiently clean (i.e., the concentration of the contaminants in the resulting mixture 252' has been reduced to a pre-specified level). If the answer may be negative, the method 600 loops back to step 650. In other words, suspended materials continue to be transported out of the vessel 210 (step 650) and processed (step 660) so as to remove contaminants. If the answer to the question in step 670 is affirmative, the method 600 may stop. Then, the vessel 210 may be removed from the current location and positioned at another location on the bottom 80 of the body of water 83, and the method 600 may be performed again. In one embodiment, after the sediment layer 270 inside the vessel 210 has been treated to a satisfactory level (i.e., the concentration of the contaminants in the resulting mixture 252' has been reduced to a pre-specified level), a contaminants map may be updated to indicate that the current location has been treated. Then, a determination may be made as to whether the current location may be the last one to be treated. If the answer is negative, the vessel 210 can be lifted and lowered to the next untreated location using a lifting device such as a crane 182 coupled to the hooks 214a and 214b. If the answer to the question is affirmative, the operation may be concluded.

Figure 3B:
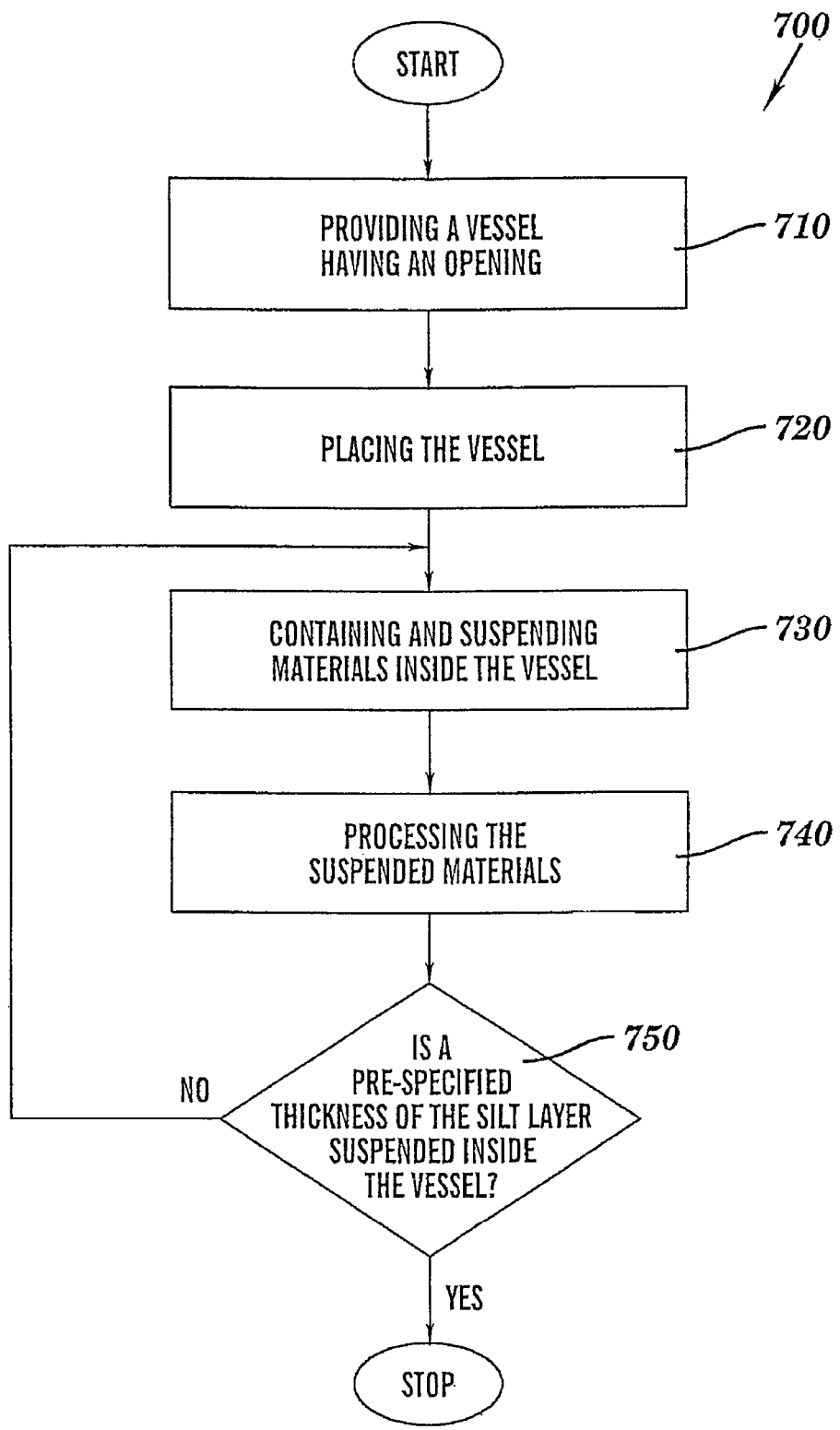
FIG. 3B illustrates a flow chart of a method for operating the apparatus of FIGS. 2A and 2B, according to embodiments of the present invention.

FIG. 3B illustrates a flow chart of a method 700 for processing contaminated material at a bottom of a body of water, the method comprising (a) providing a vessel including an opening, (b) placing the vessel such that the opening may be facing a layer of contaminated material on the bottom of the body of water and may be in direct physical contact with a top layer of the contaminated material, (c) containing and suspending, within the vessel, the contaminated material in an interior of the vessel, and (d) suspending the contaminated material until a pre-specified thickness of the top layer of the contaminated material may be suspended in the interior of the vessel. The method 700 can be used for operating the apparatus 200 of FIGS. 2A and 2B, according to embodiments of the present invention. The step 710 of the method 700 may be similar to the steps 610 of the method 600. In other words, in step 710, the vessel 210 having the opening 210' may be provided. In step 720, the vessel 210 may be placed at the first untreated location at the bottom 80 of the body of water 83, such as the river bottom.

In step 730, materials inside the vessel 210 may be contained and suspended inside the vessel 210. In one embodiment, the at least one agitating device(s) 235a, 235b, 235c, 235d, 225a, 225b, and 227 may be operated to stir up (i.e., agitate) the water 252, that may be inside vessel 210. A chemical contamination map may be used which shows how deep the sediment layer 270 may be contaminated with a certain contaminant. In step 740, the materials suspended in step 730 may be processed to eliminate the contaminants. In step 750, a determination may be made as to whether a pre-specified thickness of the sediment layer 270 may be suspended in the mixture 252' inside the vessel 210. If the answer is negative, the method 700 loops back to step 730. In other words, steps 730 and 740 may be performed until the pre-specified thickness of the sediment layer 270 may be suspended in the mixture 252' inside the vessel 210. If the answer to the question in step 750 is affirmative, the method 700 stops. After that, the vessel 210 can be lifted and placed at another untreated location 190 of the bottom 180 of the body of water 220, and the method 700 may be performed again at the other untreated location. In one embodiment, the at least one observing device(s) 205a, 205a' and 205b, 205b' can be used to monitor the thickness of the sediment layer 270 so as to determine whether agitation has reached the desired depth. For example, assume, according to the contaminant map, that at the location where the vessel 210 may be inserted into the sediment layer 270, the thickness of the sediment layer 270 may be 25 inches. Assume further that only the top 10 inches of the sediment layer 270 contain the contaminant according to the contaminant map. As a result, the at least one agitating device(s) 235a, 235b, 235c, 235d, 225a, 225b, and 227 may be allowed to operate until the at least one observing device(s) 205a, 205a' and 205b, 205b' determine that the thickness of the sediment layer 270 has been reduced to 15 inches.

In one embodiment, the step 740 of the method 700 can be similar to the step 660 of the method 600. In other words, the mixture 252' containing the suspended sediment materials can be transported out of the vessel 210 via the at least one pipe(s) 245a, 245b, and 245c for treatment. Alternatively, in step 740, the mixture 252' can be treated inside the vessel 210 instead of being transported out of the vessel 210 for processing (treatment). In one embodiment, treating chemicals can be added using the adder site 370 (FIG. 2B). As described above, the agitation and treating processes (i.e., steps 730 and 740, respectively) may be stopped when agitation reaches the desired depth.

FIG. 4 illustrates a growth packet 780 for improving the environment, according to embodiments of the present invention. The growth packet 780 may comprise an outer wall 790, that may contain plants (e.g., cuttings, roots, tubers, seeds, etc.), nutrients, and soil organisms (not shown) necessary to accelerate plant growth in a green house growing effect that shelters new growth from the forces of nature. Hereinafter, a tuber may be a stem of a plant having buds, or eyes in the axils of minute scale leaves of the tuber, wherein the buds or eyes may grow into new plants. In some embodiments, the growth packet 780 may be a "self-contained growth packet" when the outer wall 790 of the growth packet 780 may contain "self-contained growth materials" 795, such as, for example, sufficient nutrients such as fertilizers, minerals, solid support, and/or such as, for example, soil around the roots of the incipient plant for the plant to grow even though it may be placed in an otherwise sterile and barren bed, such as, for example, a barren river bed, that may be barren because it may be devoid of said self-contained growth materials 795 such as the nutrients and solid support needed for the plant to grow. In one embodiment, reinforcing strings 793 can be used to help reinforce the growth packet 780. In one embodiment, a diameter of the growth packet 780 may be from about one inch to twelve inches.

In one embodiment, the growth packet 780 can be pre-packaged as a high-energy growing pod and may have any shape such as a round shape to facilitate easy planting, for example, in the river bed.

The growth packet 780 may be pumped by systems such as the apparatuses 100 or 200 or planting systems 1000, or 3000, depicted in FIGS. 1, 2B, 6A, 9, and 10, infra, used to pump growth packets 900 and 3110 into soil whether above or below waterline as in river bottoms for soil erosion control. Plants in the growth packet 780 may be selected that have a positive tropism to light, such that the plants will grow toward the source of light and will be properly oriented for growing toward the source of light regardless whether they may be pumped into the soil root down or stem down.

In one embodiment, the growth packet 780 may be designed such that its weight makes it sink into the soil at the bottom 180 of the body of water 220, as depicted in FIG. 2A and described supra. In an alternative embodiment, the growth packet 780 can be designed such that its weight allows it to float. In one embodiment, the growth packet 780 can be equipped with an air-bladder to float as in hydroponics farming.

In one embodiment, the growth packet 780 can be filled with soil and water organisms necessary to restart damaged ecology systems such as brown field sites, slag heaps, run off ponds, lagoons, fire sites, harbors, etc.

Figure 5:
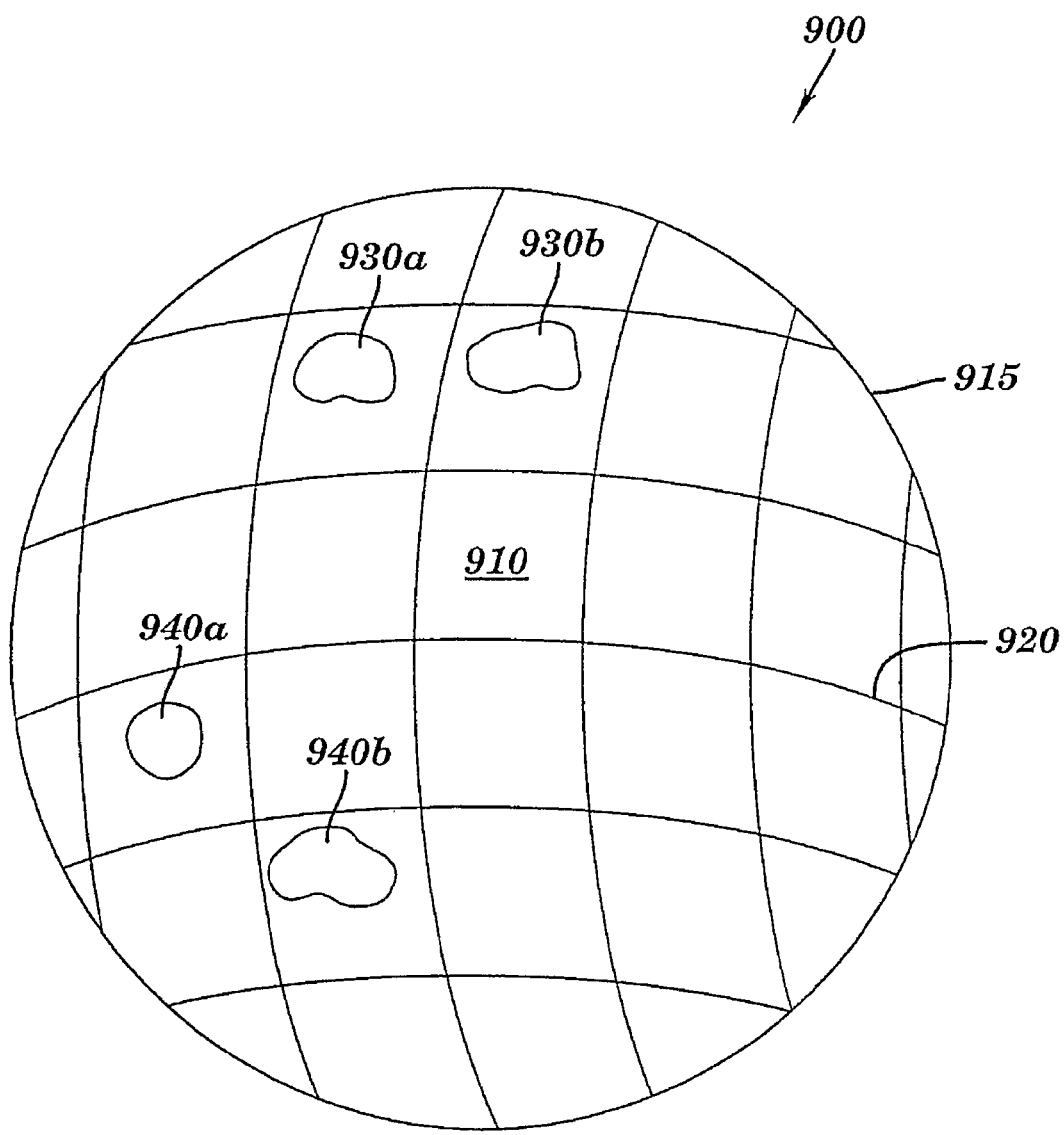
FIG. 5 illustrates a growth packet for improving the environment, according to embodiments of the present invention.

FIG. 5 illustrates a growth packet 900 for improving the environment, according to embodiments of the present invention. The growth packet 900 may comprise plants (e.g., cuttings, roots, tubers, seeds, etc.), self-contained growth materials 915 such as, for example, nutrients, and soil organisms (not shown) necessary for sustaining and accelerating self-contained plant growth within an outer wall 910. The growth packet 900 may shelter new growth from the forces of nature such as providing a green house environment, such that heat and carbon dioxide may be retained, while allowing absorption of light to generate the heat and promote photosynthesis in the plants. Self-contained plant growth may be plant growth from the growth packet 900 which may be nourished, sustained and/or accelerated by the self-contained materials 915 such as nutrients that may be inside the growth packet 900. As a result, the growth packet 900 can be used in environments where there may be insufficient nutrients in the soil to support plant growth.

In one embodiment, the outer wall 910 can be made of porous material such as burlap, such that air and fluids, such as water moisture, can be exchanged between the interior and the exterior of the growth packet 900, but the plants, self-contained materials 915 such as nutrients, and soil organisms may be confined inside the outer wall 910. A porous outer wall 910, such as one made from Burlap material, may enable plant growth to penetrate the material. In one embodiment, reinforcing strings 920 can be used to help reinforce the growth packet 900. In one embodiment, the size of the growth packet 900 may be from about one inch to twelve inches in diameter. In one embodiment, the contents inside the growth packet 900 may be in conformity with local laws, environment-friendly, and in harmony with the surrounding vegetation. In one embodiment, the self-contained materials contained inside the growth packet 900 may comprise bee plant vitamins, nutrients, pH buffers that buffer the pH from about pH=4 to about pH=10, gases such as carbon dioxide ($CO_2$), salts of phosphoric acid, pre-grown plants, and combinations thereof, that may be used to revitalize, sustain, and/or accelerate plant growth from the bottom 180 of the body of water 220, as depicted in FIG. 2A and described supra. The plant growth from the growth packet 900 may be used to replenish oxygen in waters in which oxygen has been depleted. Oxygen depletion may result from contamination of a body of water by phosphates. The phosphates may be released through urban and agricultural activities, including sewage treatment plant discharges and run-off of fertilizer from farmlands and, once in the body of water, the phosphates enable the heavy growth of algae. Algal die-off begins as the cells age, at which time the algae become very concentrated such as in early summer so that light penetration may be diminished. The dead cells fall to the bottom and may be decomposed by bacteria, which use a considerable amount of oxygen in the process necessary for fish and other life forms in the water.

In one embodiment, the growth packet 900 may comprise masses 930*a* and 930*b* scattered inside the growth packet 900. Alternatively, the masses 930*a* and 930*b* can be outside but tied to the growth packet 900. Although only two masses 930*a* and 930*b* may be illustratively shown here, in general, any number of masses like the masses 930*a* and 930*b* can be used. The masses 930*a* and 930*b* can be any objects having their weights sufficiently large so as to make the growth packet 900 sink to and stay at the bottom 180 of the body of water 220, as depicted in FIG. 2A and described supra. Once settled at the bottom 180 of the bottom of the body of water 220, plant growth from the growth packet 900 may grow upright. In one embodiment, the masses 930*a* and 930*b* can be made of a degradable material, e.g., a metal that can dissolve in the body of water 220 such that the seedlings, seeds may continue to grow in the growth packet 900, resulting in protecting the environment.

In one embodiment, the growth packet 900 may comprise floating objects 940*a* and 940*b* scattered inside the growth packet 900. Alternatively, the floating objects 940*a* and 940*b* can be outside but tied to the growth packet 900. Although only two floating objects 940*a* and 940*b* may be illustratively shown here, in general, any number of floating objects like the floating objects 940*a* and 940*b* can be used. The floating objects 940*a* and 940*b* have light weights and large volumes so as to make the growth packet 900 float. In one embodiment, the floating objects 940*a* and 940*b* can be made of a degradable material, e.g., a metal that can dissolve in the body of water 220 or a biodegradable fibrous material such as a textile material such as, for example, burlap, or starch, resulting in protecting the environment, as described supra. In one embodiment, the floating objects 940*a* and 940*b* can be air bladders. In one embodiment, multiple growth packets 900 can be tied together to form a floating habitat on the water surface.

Figure 7:
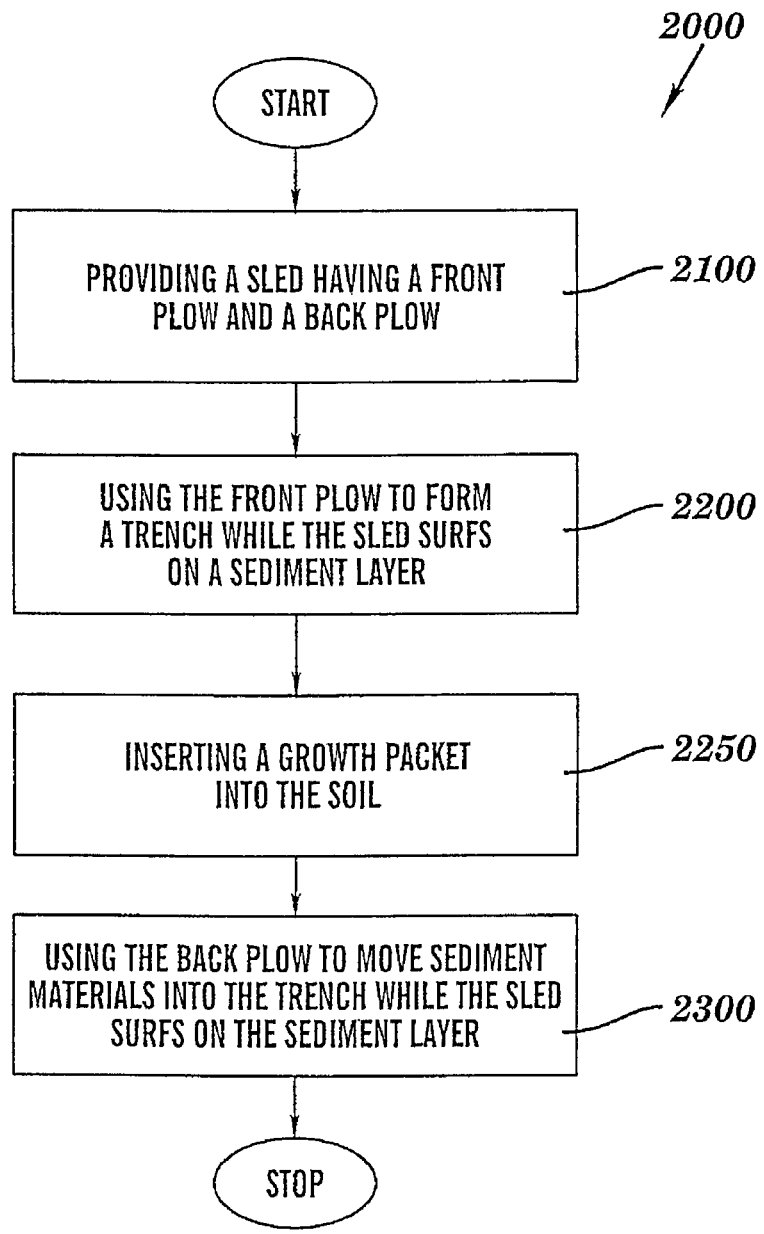
FIG. 7 illustrates a flow chart of a method for operating the planting systems, according to embodiments of the present invention.

FIG. 6A illustrates a planting system 1000 which can be used for planting the growth packet 900 of FIG. 5 into the sediment layer at the bottom 180 of a body of water 220, as depicted in FIG. 2A and described supra, in accordance with a method 2000, as depicted in FIG. 7 and described infra. Illustratively, the planting system 1000 may comprise a supporting rig 1005, such as a boat, a growth packet 900, delivery sled 1040, a growth packet pump 1010, a growth packet container 1015, a growth packet gate 1020, and a transport pipe 1025. The growth packet 900 planting sled 1040 comprises an aligning pipe 1030 operatively coupled via an extendable elbow $B_3$ to a slanted bar 1050, that may provide alignment of the aligning pipe 1030 with the guide channels 1034 along a longitudinal axis of the sled 1040, along an axis orthogonal to the longitudinal axis of the sled 1040 and/or in a direction of an arrow 1045.

Figure 6B:
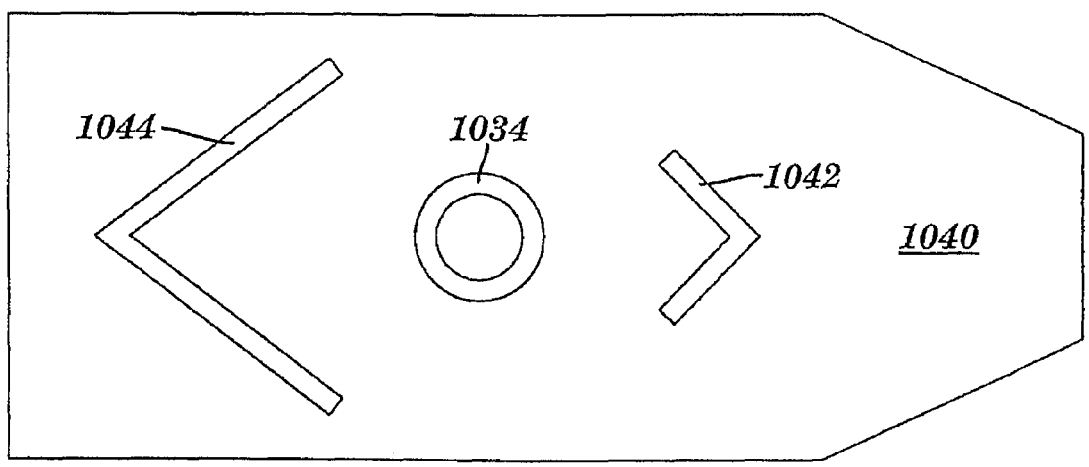
FIG. 6B illustrates FIG. 6A, including a bottom view of a planting sled of FIG. 6A, according to embodiments of the present invention.

FIG. 6B illustrates a bottom view of the planting sled 1040 of FIG. 6A. The operation of the planting system 1000 of FIG. 6A can be described infra with reference to FIG. 7 and FIG. 9.

FIG. 7 illustrates a flow chart of a method 2000 for operating the apparatus of FIG. 6A, according to embodiments of the present invention. With reference to FIGS. 6A, 6B, and 7, in the step 2100 of the method 2000, the planting sled 1040 may be operably coupled to a front plow 1042 and a back plow 1044. In the step 2200 of the method 2000, the entire planting system 1000 can be coupled to the boat 1005 such that when the boat advances, the planting sled 1040 surfs along on the bottom 180 of the body of water 220, as depicted in FIG. 2A and described supra, creating a planting trench 1033. In step 2250, a growth packet 900 may be inserted into soil, such as sediment 1070, as depicted in FIG. 6A and described supra, using an alignment sensor 3210 and ram piston 3220. Alternatively, the growth packet 900 may be inserted into soil at an edge of a body of water or soil on a shoreline adjacent to the body of water.

FIG. 9, infra, depicts the alignment sensor 3210 and the ram piston 3220 in an exploded view of a front elevation view of the planting sled 1040. In step 2300, while the planting sled 1040 surfs on the sediment layer 1070, the back plow 1044 moves sediment materials into the trench 1033. In the step 2250, the slanted bar 1050 that may be operably coupled at $B_1$ to the rig 1005 and at $B_2$ to a vertical bar 1055, may provide alignment in an x, y, and z axes of the sled 1040 wherein x and y may be the longitudinal and transverse axes in the same plane of the sled 1040 and z is the axis orthogonal to the x,y plane. In the step 2300 of the method 2000, the back plow may be used to move soil such as sediment 1070 to fill the trench 1033 and cover the growth packet 900, thereby disposing the growth packet 900 for growth.

In one embodiment, while the boat 1005 may be advancing in a direction of an arrow 1032, the gate 1020 may be periodically opened. As a result, under the pressure created by the pump 1010, any time the gate 1020 opens, one or more growth packets 900 may be pushed into the transport pipe 1025, through the alignment pipe 1030, and into the soil (i.e., sediment layer 1070) at the bottom 180 of the body of water 220, as described in FIG. 2A and described supra, via the opening 1034. In one embodiment, the transport pipe 1025 may be flexible so that the relative positions of the container 1015 and the alignment pipe 1030 can change while the planting sled 1040 which can be tightly coupled to the alignment pipe 1030 surfs on the bottom 180 of the body of water 220, such as a river bottom.

In one embodiment, while the planting sled 1040 slides on the sediment surface 1065, the plows 1042 and 1044 may be dragged in the sediment layer 1070. The front plow 1042 dashes through the sediment materials and forms a trench 1033 along its path. The back plow 1044 moves after the front plow 1042 and moves sediment materials displaced by the front plow 1042 back into the trench 1033. As a result, whenever a growth packet 900 exits the alignment pipe 1030 via the opening 1034, the growth packet 900 may be planted in the trench 1033 dug by the front plow 1042. Then, the back plow 1044 fills the trench 1033 with sediment materials burying the growth packet 900 in the trench 1033 in the process.

In one embodiment, the front plow 1042 extends deeper into the sediment layer 1070 than the back plow 1044. As a result, when the growth packet 900 may be dropped at the bottom of the trench 1033, formed by the front plow 1042, the growth packet 900 may be below the sweep of the back plow 1044 making it easier for the back plow 1044 to bury the growth packet 900 in the trench 1033.

If it may be desired to move the planting sled 1040 up a slope, the vertical bar 1055 may be drawn up by the hydraulic pump 1060 so as to enable the slanted bar 1050 that may be operably coupled to the boat 1005 to rotate around an axis $B_1$. As a result, the planting sled 1040 can slide uphill. The vertical bar 1055 sliding in the sliding pipe 1060 which can be operably coupled to the boat 1005 provides the force to move the planting sled 1040, as in surfing, along the soil of the bottom of the body of water, such as the sediment 1070.

Similarly, if it may be desirable to move the planting sled 1040 down a slope, the slanted bar 1050 may be lowered by the hydraulic pump 1060 and the vertical bar 1055 so as to enable the slanted bar 1050 to rotate on the axis $B_1$. Alternatively, the vertical bar 1055 may be pushed down by a spring loaded mechanism to exert a downward force on the slanted bar 1050. As a result, the planting sled 1040 can slide downhill.

In one embodiment, a GPS (Global Positioning System) 1075 can be used with the planting system 1000 so as to ensure that the structures 900 may be planted at the desired locations at the bottom 180 of the body of water 220, such as a river bottom, as depicted in FIG. 2A and described supra. In other words, the use of the GPS 1075 helps the operator of the planting system 1000 keep track of the locations of the river bottom that have been planted with growth packet 900. As a result, pre-specified areas of the river bottom can be revitalized by implanting the structures 900 using the planting system 1000.

In one embodiment, a sonar device 1080 can be used with the planting system 1000 to help the operator of the planting system 1000 recognize obstacles at the bottom 180 of the body of water 220, such as a river bottom, as depicted in FIG. 2A and described supra. As a result, the operator can steer the planting sled 1040 around the obstacles (e.g., rocks, debris, etc.) at the bottom 180 of the body of water 220, so as to avoid damage to the planting sled 1040.

In the embodiment described above, the slanted bar 1050 may be directly coupled to the alignment pipe 1030. Alternatively, the slanted bar 1050 can be directly coupled to the planting sled 1040.

Figure 8A:
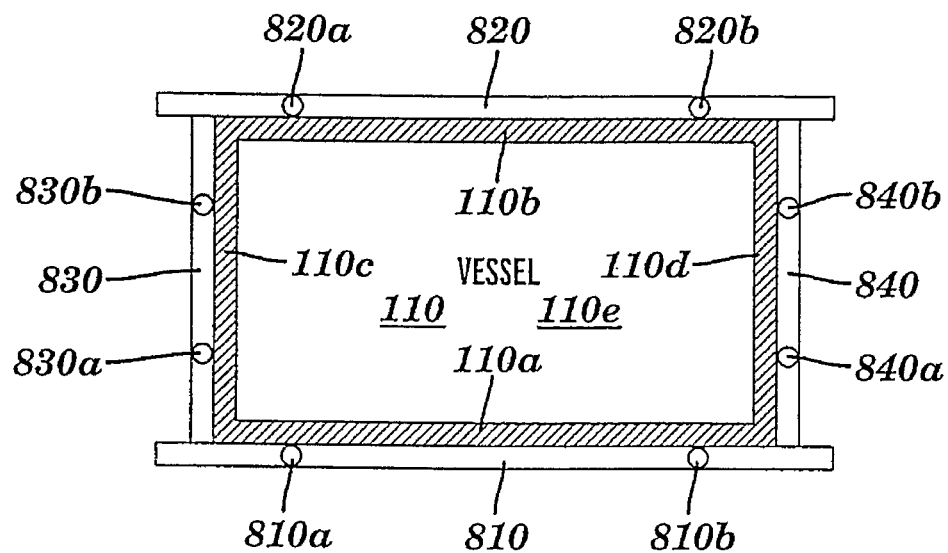
FIG. 8a illustrates a top view of the vessel of FIG. 1, coupled to four curtain plates, according to embodiments of the present invention.
Figure 8B:
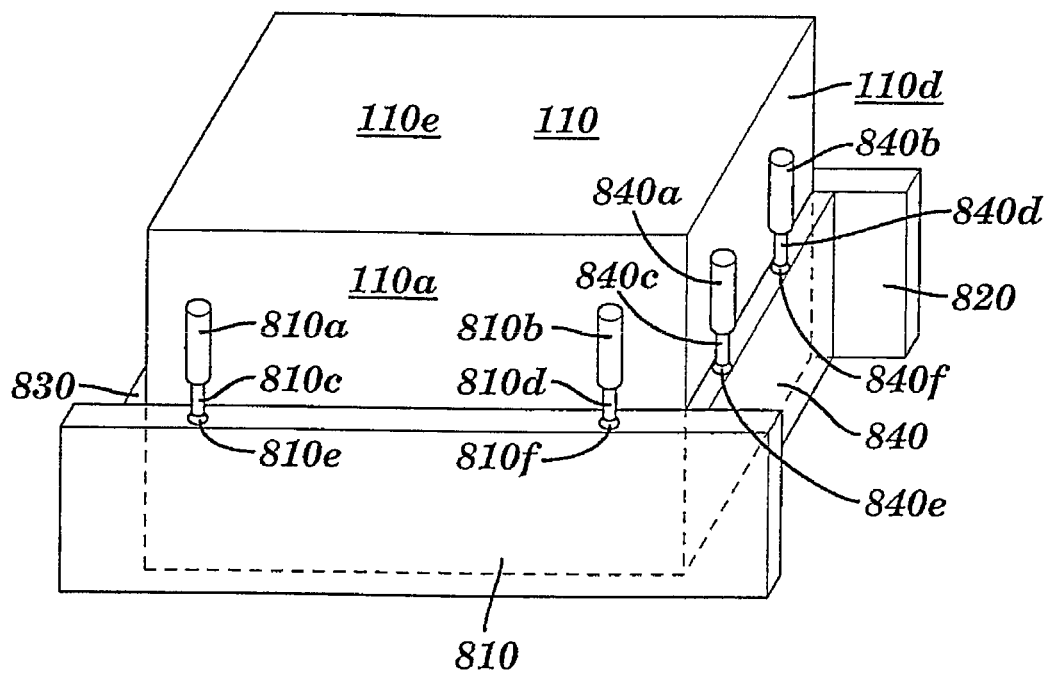
FIG. 8b illustrates a perspective view of the vessel and the curtain plates of FIG. 8a, according to embodiments of the present invention.
Figure 8C:
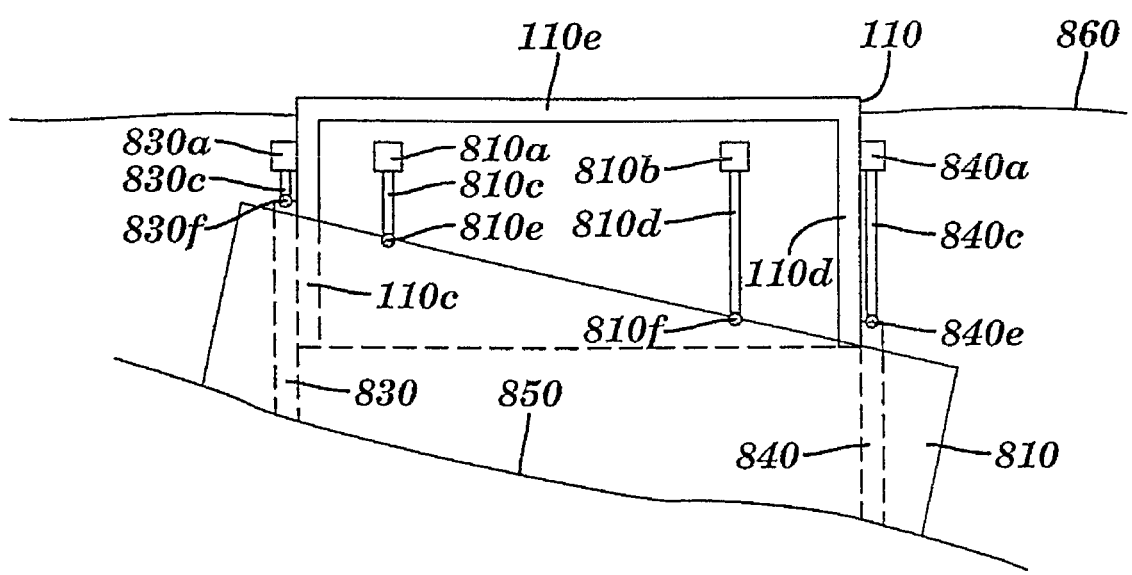
FIG. 8c illustrates a side view of the vessel and the curtain plates of FIG. 8a, after the curtain plates have been lowered to the bottom of a body of water, according to embodiments of the present invention.

FIGS. 8a-c illustrate a top view of the vessel (or vessel) 110 of FIG. 1 comprising a top plate 110e and four side plates 110a, 110b, 110c, and 110d abutting and being coupled to four curtain plates 810, 820, 830, and 840, respectively, according to embodiments of the present invention. In one embodiment, each of the four curtain plates 810, 820, 830, and 840 may be coupled to a pair of hydraulic rams which in turn may be coupled to the vessel 110. More specifically, the curtain plate 810 may be coupled to rams 810a and 810b. The curtain plate 820 may be coupled to rams 820a and 820b. The curtain plate 830 may be coupled to rams 830a and 830b. The curtain plate 840 may be coupled to rams 840a and 840b.

FIGS. 8a-c illustrate a perspective view of the vessel 110 and the curtain plates 810, 820, 830, and 840 of FIGS. 8a-c, according to embodiments of the present invention. The curtain plate 810 may be coupled to the hydraulic ram 810a via a single-plane connector 810e and a piston 810c. In addition, the curtain plate 810 may be coupled to the hydraulic ram 810b via a single-plane connector 810f and a piston 810d.

In like manner, the curtain plate 840 may be coupled to the hydraulic ram 840a via a single-plane connector 840e and a piston 840c. In addition, the curtain plate 840 may be coupled to the hydraulic ram 840b via a single-plane connector 840f and a piston 840d. The curtain plate 840 may be coupled to the hydraulic ram 840a, 840b via a single-plane connector 840e, 840f and a piston 840c, 840d. The piston 840c, 840d may be capable of sliding in and out inside the ram 840a, 840b. The single-plane connector 840e, 840f may be tightly coupled to one end of the piston 840c, 840d. As a result, the single-plane connector 840e, 840f can move only up and down while the piston 840c, 840d moves up and down inside the ram 840a, 840b.

Similarly, the curtain plate 810 may be coupled to the hydraulic ram 810b via a single-plane connector 810f and a piston 810d. The piston 810d may be capable of sliding in and out inside the ram 810b. The single-plane connector 810f may be tightly coupled to one end of the piston 810d. As a result, the single-plane connector 810f can move only up and down while the piston 810d moves up and down inside the ram 810b.

In one embodiment, each of the single-plane connectors 810e and 810f only enables the curtain plate 810 to rotate around it in a plane parallel to the side plate 110a of the vessel 110. As a result, by adjusting the pistons 810c and 810d, the curtain plate 810 can be pulled up, lowered down, and rotated around a plane parallel to the side plate 110a of the vessel 110. In one embodiment, the other three curtain plates 820, 830, and 840 may be coupled to the vessel 110 in a similar manner.

In one embodiment, the curtain plate 810 may be longer in length than its abutting side plate 110a of the vessel 110. Similarly, the curtain plate 820 may be longer in length than its abutting side plate 110b (FIG. 8a-c) of the vessel 110. However, the curtain plates 830 and 840 may be of the same length as their abutting side plates 110c and 110d, respectively, of the vessel 110.

FIG. 8a-c illustrate the use of the four curtain plates 810, 820, 830, and 840 for extending the side plates 110a, 110b, 110c, and 110d, respectively. In one embodiment, the vessel 110 may be lowered into a body of water but its top plate 110e may be kept above the water surface 860. Then, the four curtain plates 810, 820, 830, and 840 may be lowered down until they come into contact with the bottom of the body of water such that the vessel 110 and the curtain plates 810, 820, 830, and 840 form with the bottom of the body of water an enclosed space inside the vessel 110. In other words, the four curtain plates 810, 820, 830, and 840 serve as extensions of the side plates 110a, 110b, 110c, and 110d of the vessel 110, respectively.

In one embodiment, the vessel 110 may be positioned in the body of water such that its top plate 110e may be either submerged or un-submerged and may be parallel to the water surface 860 of the body of water, and such that the slope direction of the bottom 850 of the body of water underneath the vessel 110 may be from the curtain plate 830 to the curtain plate 840. A slope direction of a plane may be defined to be the direction of movement of a ball when let to roll freely on the plane under the effect of gravity. Then, the two curtain plates 830 and 840 can be lowered down vertically until they come into complete contact with the bottom 850 of the body of water. Each of the two curtain plates 810 and 820 can be lowered vertically and rotated clockwise in a plane parallel to its abutting side plate 110a or 110b until it comes into complete contact with the bottom 850 of the body of water. As a result of the curtain plates 810 and 820 being longer in length than the side plates 110a and 110b, respectively, the curtain plates 810 and 820 can rotate to completely contact the bottom without creating an opening on the side of the vessel 110, as shown in FIG. 8a-c.

In one embodiment, each of the rams 810a and 810b can rotate in a plane parallel to the side plate 110a around a point tightly affixed to the vessel 110. As a result, the curtain plate 810 can be moved horizontally by simultaneously rotating both the rams 810a and 810b. This adds further flexibility in movement of the curtain plate 810.

In one embodiment, similarly, each of the rams 820a and 820b can rotate in a plane parallel to the side plate 110b around a point tightly affixed to the vessel 110. As a result, the curtain plate 820 can be moved horizontally by simultaneously rotating both the rams 820a and 820b. This adds further flexibility in movement of the curtain plate 820.

In the embodiments described above, the connectors 830a and 830b associated with the curtain plate 830 and the connectors 840a and 840b associated with the curtain plate 840 may be of single-plane type. Alternatively, these connectors 830a, 830b, 840a, and 840b can be omitted. In that case, the curtain plates 830 can be soldered to the pistons 830a and 830b, and the curtain plates 840 can be soldered to the pistons 840a and 840b.

In one embodiment, the curtain plates 810, 820, 830, and 840 and associated components (connectors, rams, and pistons) can be made of a stainless material. Their sizes may be sufficient to withstand the expected maximum forces exerted upon them.

FIG. 9 depicts an exploded side elevation view of the planting sled 1040, as depicted in FIG. 6A, supra, and described in associated text, illustrating an alignment sensor 3210 and a ram piston 3220, wherein the alignment sensor 3210 may be operatively coupled to the ram piston 3220. The alignment sensor 3210 may be used for aligning the ram piston 3220 with the at least one growth packet channel 1034, wherein the alignment sensor 3210 may be located on a tip of the ram piston 3220 and the ram piston 3220 may be manually or computer controlled. The ram piston 3220 may slide within the aligning pipe 1030, wherein the aligning pipe 1030 may be positioned manually, by an operator, or in an automated fashion, by the computer, anywhere along the xyz coordinates of the planting sled 1040. The alignment sensor 3210 may be used for aligning the ram piston 3220 with the growth packet 900 channel 1034. A purpose of the aligned ram piston 3220 may be to physically and directly drive the growth packet 900 through the channel 1034, inserting the growth packet 900 into the trench 1033 that may have been made by movement of the forward plow 1042 in the direction of the arrow 1032 in the soil of the bottom 1065 of the body of water 1037, such as sediment 1070, as depicted in FIG. 6A, and described herein. Alternatively, the ram piston 3220 may be used to physically and directly insert the growth packet 900 into soil on a shore alongside the body of water 1037 such as a river or into soil at an edge of the body of water 1037 and the shore. The alignment sensor 3210 and the ram piston 3220 may be aligned with the at least one growth packet guide channel 1034, in accordance with the step 2250 of the method 2000, as depicted in FIG. 7 and described supra.

FIG. 10 depicts a Blanket Roll Planting System (BR Planting System) 3000, comprising: a rig or boat 3095, a blanket roll 3030, a control 3010, a supporting system 3050, and a ram piston 3020. The control 3010 may be a computer, wherein the computer may be operably connected to an aligning sensor 3015 of the ram piston 3020, such as the alignment sensor 3210, as depicted in FIG. 9 and described supra, for aligning the trajectory of the ram piston 3020 in the direction of the arrow 3160 to drive the stakes 3080 to designated locations 3070 in the blanket roll 3030 and 3140 in the soil 3130. Alternatively, the control 3010 may be a manual control, wherein the alignment sensor 3015, such as the alignment sensor 3210, as depicted in FIG. 9 and described supra, may provide a visual image of the alignment of the ram piston 3020 with the blanket roll 3030 to an operator. The blanket roll 3030 may include at least one growth packet 3110 incorporated in a material such as the burlap or other biologically degradable material used to house the growth packets 900, as depicted in FIG. 5, and described supra. The blanket roll 3030 may be any appropriate dimensions, such as from about one to one thousand feet long and from about six inches to about ten feet wide. The growth packets 3110 may be any appropriate dimensions, such as from about one to about twelve inches in diameter. The growth packet 3110 may contain plants (e.g., cuttings, roots, tubers, seeds, etc.), nutrients, and soil organisms (not shown) for accelerating growth in a green house growing effect that shelters new growth from the forces of nature. Hereinafter, a tuber may be a stem of a plant having buds, or eyes in the axils of minute scale leaves of the tuber, wherein the buds or eyes may grow into new plants. In some embodiments, the growth packet 3110 may be a "self-contained growth packet" with an outer wall that may contain self-contained materials such as sufficient nutrients such as fertilizers, minerals, solid support, such as soil around the roots of the incipient plant for the plant to grow even though it may be placed in an otherwise sterile and barren bed, such as, for example, a barren river bed, that may be barren because it may be devoid of said nutrients and solid support needed to sustain or accelerate plant growth. In like manner as described for the growth packets 780 and 900, the blanket roll 3030 may provide nourishment such as nitrate and phosphate containing fertilizer for the growth packets 3110 to receive nourishment after they may be inserted into soil.

The stake and growth packet delivering system 3050 may be secured at a location 3093 to the rig or boat 3095 via connecting tether 3092. The connecting tether 3092 may be flexible material such as rope or plastic or rigid, such as metal ties. The stake and growth packet delivering system 3050 may comprise a stake supply 3090, a stake delivery pipe 3100, wherein stakes 3090 may move in a direction of an arrow 3150 into a trajectory of a ram piston 3020, designated by a direction of an arrow 3160, and a blanket roll guide system 3060, wherein the blanket roll guide system 3060 guides the laying of the blanket roll 3030, such that the blanket roll 3030 may pass through the trajectory of the ram piston 3020, in the direction of the arrow 3160. The stakes 3090 and 3080 may be made of wood, plastic, composites, such as of plastic and rubber, or metal, and may be oblong with pointed ends to facilitate entry into the soil. Alternatively, the stakes may be any appropriate solid geometric shape for penetrating the blanket roll 3030 at a location 3070 and securing the blanket roll to the soil at a location 3140. The roll guide system 3060 may be a wheel that may include a groove on which the blanket roll slides, or any appropriate mechanism for guiding the blanket roll 3030.

The ram piston 3020 may be hydraulic or spring powered and may include an alignment sensor 3015 and an alignment pipe 3040 for aligning the ram piston 3020, such that the trajectory of the ram piston 3020, designated by the direction of the arrow 3160, may drive the stakes 3080 to designated locations 3070 in the blanket roll 3030 and 3140 in the soil 3130. In the method 4100 of the method for planting 4000, depicted in FIG. 11 and described infra, the control 3010 may receive feedback from the alignment sensor 3015 to align the ram piston 3020 trajectory to drive the stakes 3080 to designated locations 3070 in the blanket roll 3030 and 3140 in the soil 3130. Alternatively, the control 3010 may be a manual control, wherein the alignment sensor 3015, such as the alignment sensor 3210, as depicted in FIG. 9 and described supra, may provide a visual image of the alignment of the ram piston 3020 such that an operator may align the ram piston 3020 trajectory to drive the stakes 3080 to designated locations 3070 in the blanket roll 3030 and 3140 in the soil 3130. Supporting rods 3170 may be operably coupled to the aligning pipe 3040 and roll guide system 3060, resulting in maintaining a constant trajectory of the ram piston 3020 in the direction of the arrow 3160, even if a rate of feeding the blanket roll 3030 increases, such that resistance to feeding of the blanket roll 3030 may create a force orthogonal to the direction of the arrow 3160.

Figure 11:
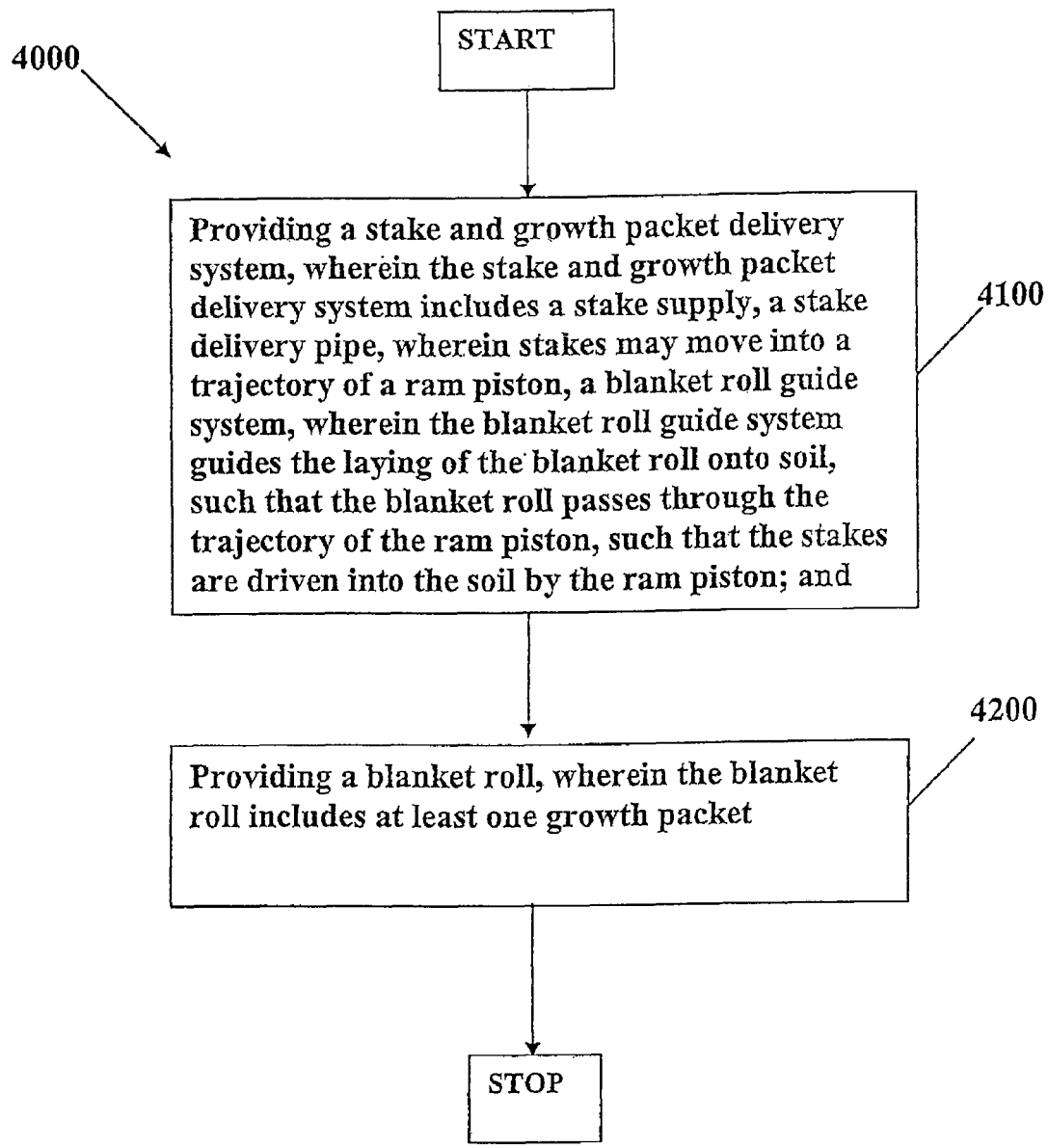
FIG. 11 illustrates a method for planting using a ram piston, according to embodiments of the present invention.

FIG. 11 depicts a method 4000 for planting using the a Blanket Roll Planting System (BR Planting System) 3000, as depicted in FIG. 10, supra, and described herein. In the step 4100 of the method 4000, a stake and growth packet delivery system 3050 may be provided, wherein the stake and growth packet delivery system 3050 may include a stake supply 3090, a stake delivery pipe 3100, a ram piston 3020, having a trajectory in the direction of the arrow 3160, a blanket roll guide system 3060, wherein the blanket roll guide system 3060 guides the laying of the blanket roll 3030 onto the bottom 3130 of the body of water 3120, such as soil or sediment, such that the blanket roll 3030 passes through the trajectory of the ram piston 3020, in the direction of the arrow 3160, such that the stakes 3080 may be driven into the blanket roll 3030 and bottom of the body of water 3130 by the ram piston 3020. In the step 4200 of the method 4000, a blanket roll 3030 may be provided to the stake and growth packet delivery system 3050, wherein the blanket roll 3030 may include at least one growth packet 3110. In the step 4200, the blanket roll 3030 may be transported to the planting site pre-loaded with the at least one growth packet 3110 or it may be transported to the planting site as an empty casing and loaded with the at least one growth packet 3110 as needed. The blanket roll 3030 of the BR Planting System 3000 may be unrolled from a support system 3050 and staked down into position in the bottom 3130 of the body of water 3120, such as the sediment, in deep or shallow water. Alternatively, the blanket roll 3030 may be staked down on a river bank, a shore of a lake or river, or at an edge of a body of water 3120. The support system 3050 can be mounted on barges or boats for laying the blanket roll 3030 into the soil bottom 3130 of a body of water 3120, such as the sediment, in deep or shallow water. Alternatively, the support system 3050 may be mounted to trucks, crawlers, excavators etc., or boats for laying the blanket roll 3030 into the bottom 3130 of a body of water 3120 such as soil of a river bank, a shore of a lake or river, or at an edge of the body of water 3120.

FIG. 12 depicts a longitudinal cross section of the apparatuses 100 or 200, illustrating an exploded view of the attachment 248" depicted within the circle having an intermittent perimeter 12, 14 in FIG. 2A, supra, wherein the attachment 248" may be a fluted filter. The attachment 248", that may be a fluted filter, may comprise a bore 260, a fluted surface 265 having at least one peak(s) 263 and at least one valley(s) 259, and at least one channel(s) 267, wherein the at least one channel(s) 267 may extend from the fluted surface 265 in the at least one valley(s) 259 into the bore 260 of the attachment 248". The attachment 248", that may be a fluted filter, may be operatively coupled to the at least one pipe(s) 248 at an opening 248', as depicted in FIG. 2A, supra. Hereinafter, "operatively coupled" means the bore 260 of the attachment 248" may be contiguous with the opening 248' of the at least one pipe(s) 248, such that material, such as contaminated water and suspended contaminated sediment in the mixture 252' may pass from the interior 252 of the vessel 210 through at least one channel(s) 267 of the attachment 248" into the at least one pipe(s) 248 in a direction of the arrow 177, as depicted in FIGS. 2A and 2B, and described supra. Alternatively, the attachment 248" that may be a fluted filter, may be operatively coupled to the at least one pipe(s) 245a, 245b, or 245c of the apparatus 200, as depicted in FIG. 2A, or to the at least one pipes 145a', 145b' or 145c' of the apparatus 100, as depicted in FIG. 1. The attachment 248", such as the fluted filter, may be made of plastic, rubber, composites, such as plastic and rubber, metal, wherein the metal may be copper, brass, stainless or carbon steel. The at least one peak(s) 263 of the fluted surface 265 may be a point or be blunt shaped.

Figure 13:
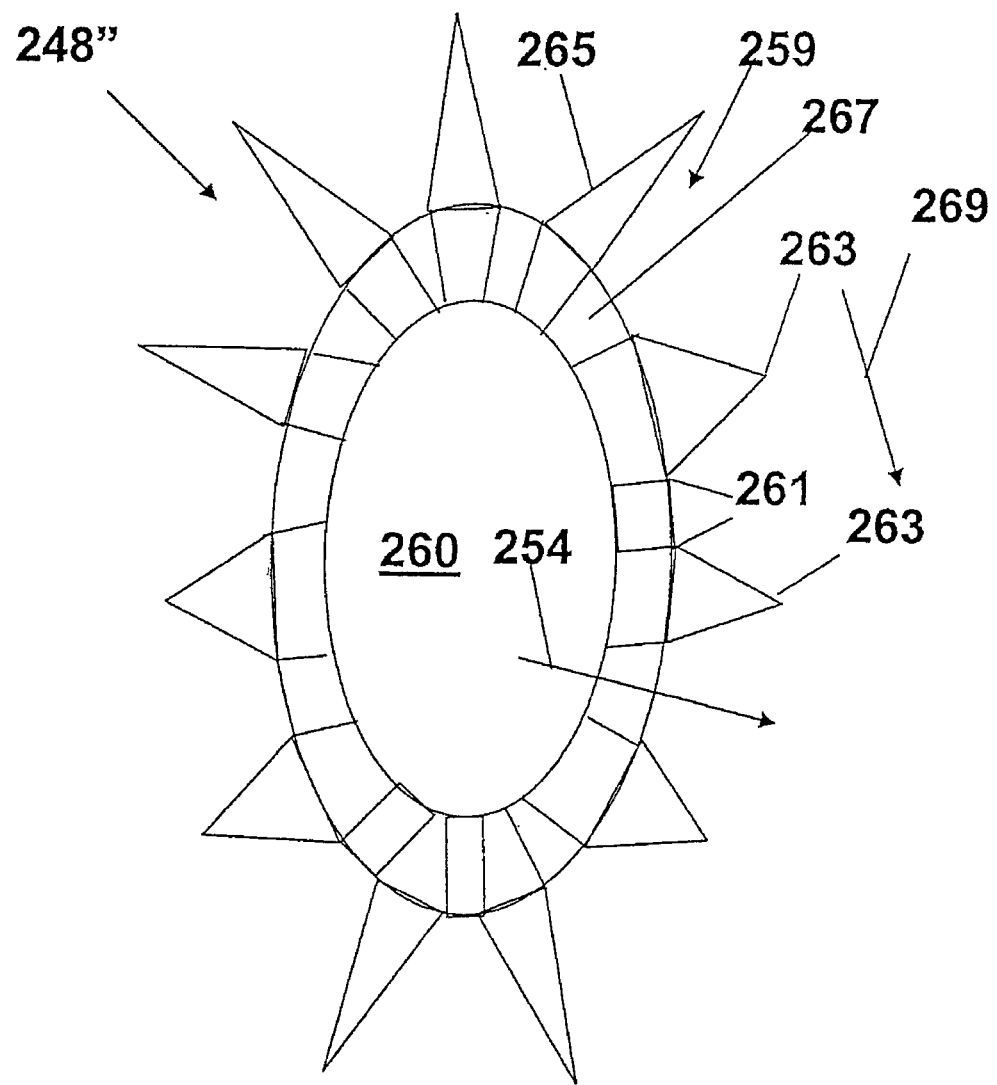
FIG. 13 depicts a transverse cross-sectional view of the apparatus, illustrating an exploded view of an attachment, as depicted in FIG. 2A, supra, according to embodiments of the present invention.

FIG. 13 depicts a transverse cross-sectional view of the attachment 248" that may be a fluted filter. In FIG. 13, a length in a direction of an arrow 269 between the adjacent peaks 263 of the fluted surface 265 may be from about 1 in. to about 3 inches. In one embodiment, the at least one channel(s) 267 may have a diameter from about 0.002 mm to about 0.006 mm and a length in the direction of the arrow 177 between adjacent points 261 of the fluted surface may be from about 0.002 mm to about 0.006 mm. In another embodiment, the at least one channel(s) 267 may have a diameter from about 0.006 mm to about 0.02 mm and a length in the direction of the arrow 177 between adjacent points 261 of the fluted surface may be from about 0.006 mm to about 0.02 mm. In another embodiment, the at least one channel(s) 267 may have a diameter from about 0.02 mm to about 0.063 mm and a length in the direction of the arrow 177 between adjacent points 261 of the fluted surface may be from about 0.02 mm to about 0.063 mm. The fluted surface 265 between the at least one points 263 and 261 may be a smooth linear surface, or alternatively the fluted surface 265 may be rough or non-uniform. Adjacent points 261 may align or be coincident with opposite points along a diameter of the at least one channel(s) 267. A purpose of the attachment 248", that may be the fluted filter, may be to remove or filter out solids having a larger diameter than the length between the adjacent peaks 263 of the fluted surface 265 of the attachment 248". In one embodiment, the attachment 248", that may be the fluted filter, may remove or filter out solid material in the mixture 252', thereby preventing solids such as rocks or other insoluble solid debris, that may have been carried along with the contaminated material such as contaminated sediment in the mixture 252' in the interior 252 of the vessel 210 from entering the at least one channel(s) 267 and the at least one pipe 248. It has been found that at least one channel(s) 267 may become occluded or clogged with solids having a greater diameter than the at least one channel(s) 267, and that using the valleys 259 to screen such solids, such that the length between opposite coplanar points, in the plane of the arrow 177 lessens as the solids approach the at least one channel(s) 267.

Figure 14:
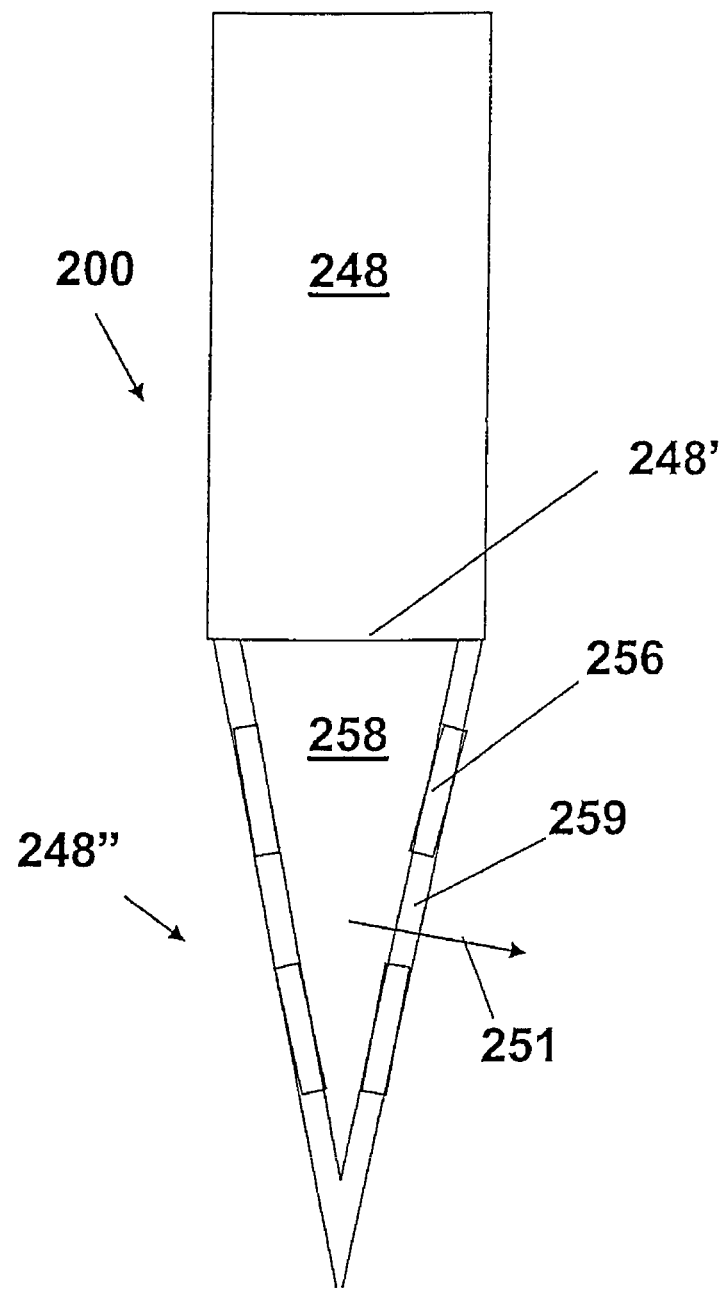
FIG. 14 depicts a longitudinal cross sectional view of the apparatus, illustrating an exploded view of an attachment, as depicted in FIG. 2A, supra, according to embodiments of the present invention.

FIG. 14 depicts a longitudinal cross-sectional view of the apparatus 200, illustrating an exploded view of the attachment 248" when the attachment 248" may be a coarse filter. The attachment 248", such as the coarse filter, as depicted in FIG. 14, comprises a filter element 258, wherein the filter element 258 may include a screen 259 and at least one orifice 256 in the screen 259, and wherein the at least one orifice 256 may have a diameter from about ⅛ in. to about 1 in. The at least one orifice 256 may be round, square, rectangular or any appropriate polygon. The at least one orifice 256 of the apparatus 248" that may be a coarse filter may be an array of holes having a diameter from about ⅛ to about 1 in. The filter element 258 may be conical shaped as in FIG. 14, or alternatively, the filter element 258 may be spherical, cubic, pyramidal, or any solid geometric shape of a polygon. The filter element 258 may be any appropriate solid material such as sheet metal, plastic, wherein the sheet metal may be copper, zinc, stainless steel or carbon steel, or any sheet material that may be non-porous to water, sediment or solid objects such as rocks or pebbles in the body of water 220.

In FIG. 14, the attachment 248", that may be a coarse filter, may be operatively coupled to the at least one pipe(s) 248 at an opening 248', as depicted within the circle having an intermittent perimeter 12, 14 in FIG. 2A, supra. Hereinafter, "operatively coupled" means the bore 258 of the attachment 248" may be contiguous with the opening 248' of the at least one pipe(s) 248, such that material, such as contaminated water and suspended contaminated sediment in the mixture 252' may pass from the interior 252 of the vessel 210 through the at least one orifice(s) 256 of the apparatus 248" into the at least one pipe(s) 248 in a direction of the arrow 177, as depicted in FIGS. 2A and 2B, and described supra.

Referring to FIGS. 2A and 2B, and FIGS. 12-14, it has been found that materials or solids in the body of water 220, as depicted in FIGS. 2A and 2B, supra, such as suspended sediment in the mixture 252' may occlude or clog the at least one channel(s) 267 or the at least one orifice(s) 256 of the attachment 248" when the attachment 248" of the apparatus 200 is a fluted filter or coarse filter. Referring to FIG. 13, it has been found that the occlusions or clogs may be removed from the at least one channel(s) 267 of the attachment 248", when the attachment 248" may be a coarse filter, by pumping, e.g., with pump 380, the mixture 252' such that the mixture 252' in the "open or closed" piping system 188 may be forced in a direction of the arrow 254, as depicted in FIG. 13, through the at least one channel(s) 267 of the attachment 248".

Referring to FIG. 14, it has been found that the occlusions or clogs may be removed from the at least one orifice(s) 256 of the attachment 248", when the attachment 248" may be a fluted filter, by pumping, e.g., with pump 380, the mixture 252' such that mixture 252' in the "open or closed" piping system 188 may be forced in a direction of the arrow 251, as depicted in FIG. 14, through the at least one orifice(s) 256 of the attachment 248". Alternatively, an untrasonic generator may be operatively coupled to the attachment 248" to provide bursts of ultrasonic vibration to remove occlusions or clogs from the at least one channel(s) 267 or the at least one orifice(s) 256, of the attachment 248", when the attachment 248" may be a fluted filter or coarse filter.

Figure 15:
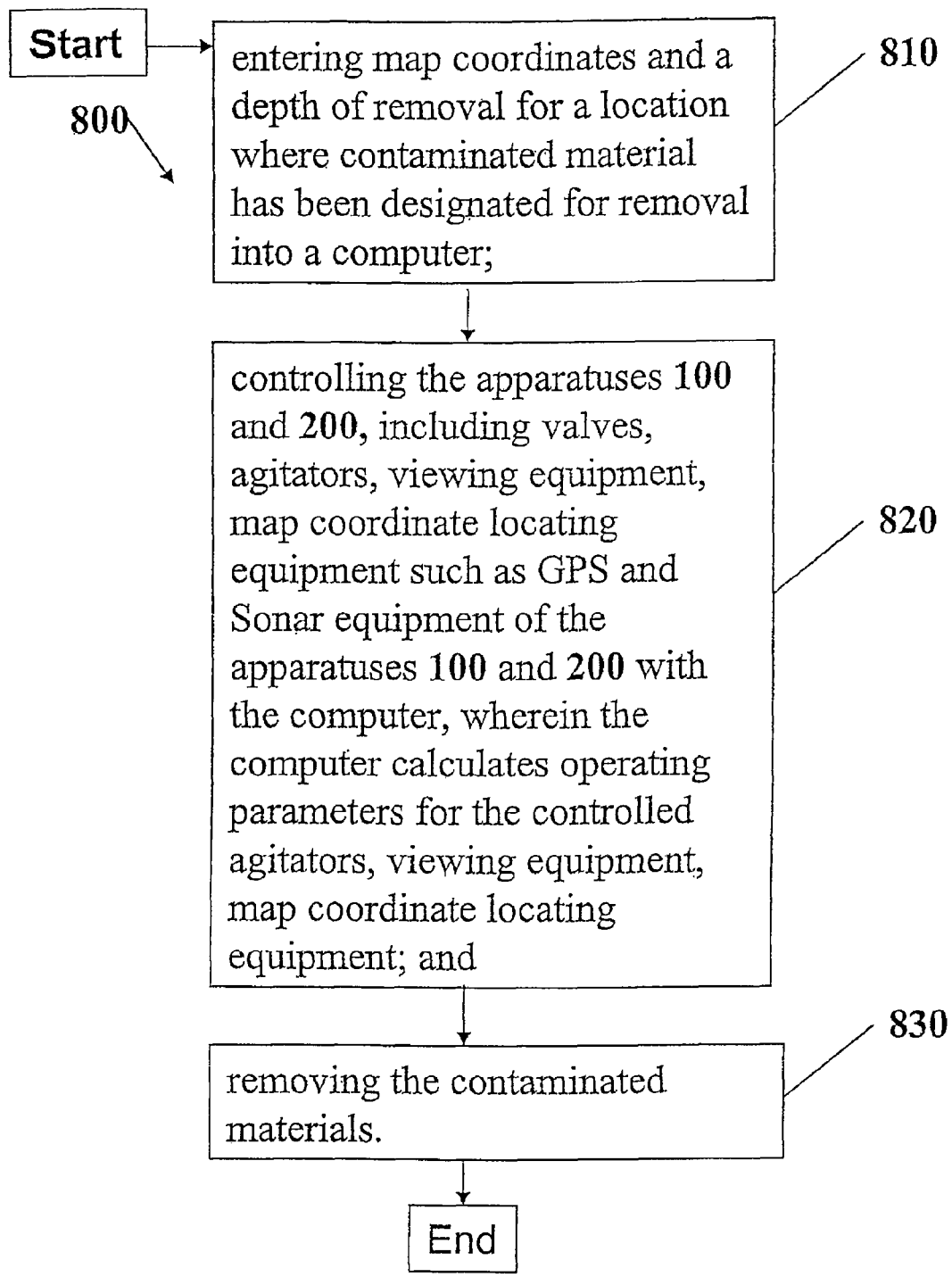
FIG. 15 depicts a flow chart illustrating an automated method of operating the apparatuses as depicted in FIGS. 1, 2A and 2B, according to embodiments of the present invention.
Figure 16:
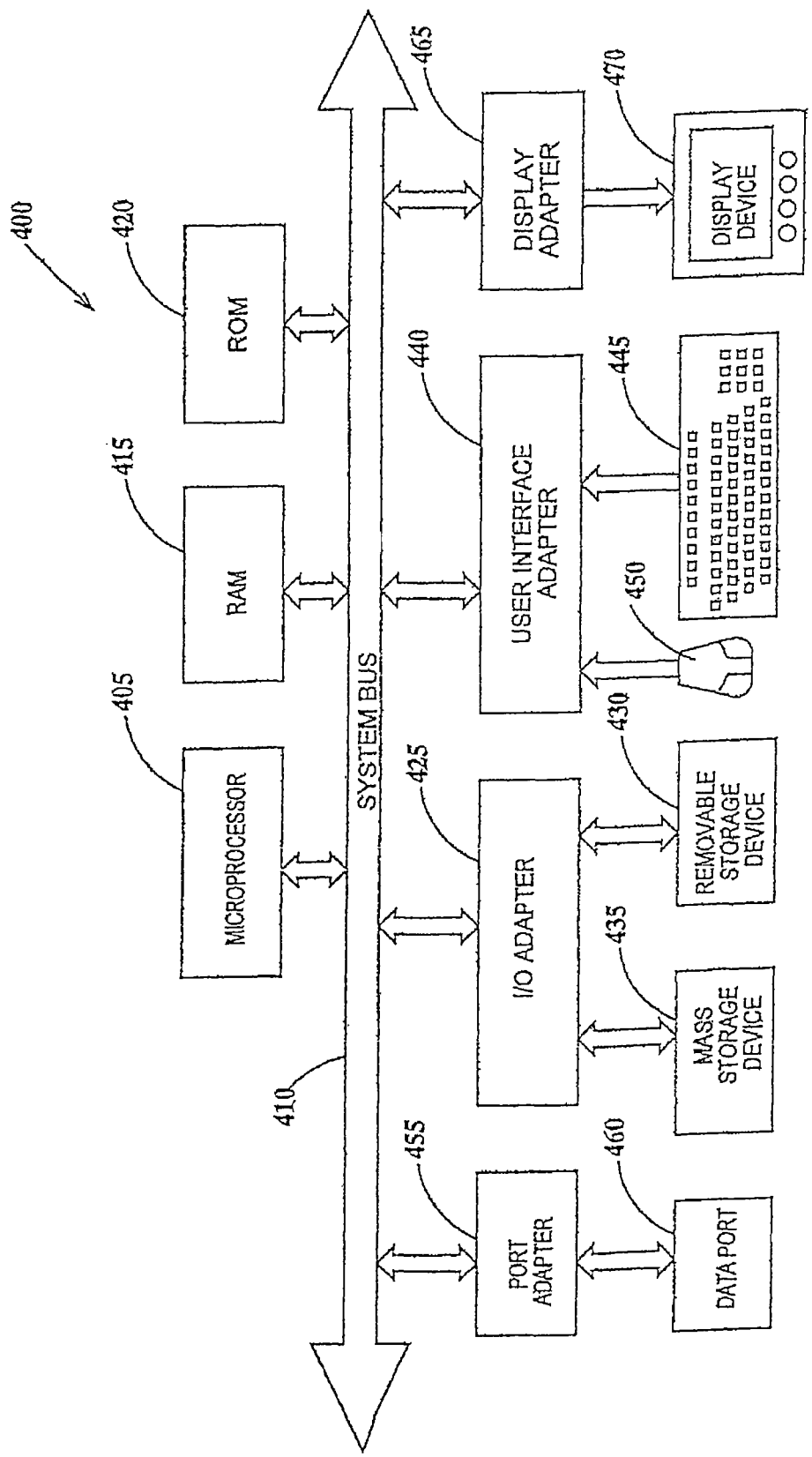
FIG. 16 depicts a schematic block diagram of a computer for automatically operating the apparatuses as depicted in FIGS. 1, 2A and 2B, according to embodiments of the present invention.

FIG. 15 depicts an overall flowchart of a method 800 for operating the apparatuses 100 and 200 robotically, wherein the valves, agitators, viewing equipment, map coordinate locating equipment such as GPS and Sonar equipment may be remotely computer controlled such as by remotely placing the valves in open or closed positions in the piping systems 45 and 188 for the apparatuses 100 and 200. The terms "enter and entering" are defined to mean typing through a keyboard (or moving or clicking a pointing device) linked to a computer 400, as depicted in FIG. 16, infra and described herein, adapted to display the information entered on a screen. The method 800 comprises: a the step 810, wherein the operator enters map coordinates and a depth of removal for a location where contaminated material has been designated for removal; a step 820, controlling the apparatuses 100 and 200, including valves, agitators, viewing equipment, map coordinate locating equipment such as GPS and Sonar equipment of the apparatuses 100 and 200 with the computer 400, wherein the computer 400 calculates operating parameters for the controlled agitators, viewing equipment, map coordinate locating equipment; and a step 830, wherein the apparatuses 100 and 200 remove the contaminated materials.

Generally, the method 800 described herein with respect to removing contaminated materials illustrated in FIGS. 3A, 3B, and 10 and described supra, may be practiced with a general-purpose computer 400 and the method may be coded as a set of instructions on removable or hard media for use by the general-purpose computer 400. FIG. 16 is a schematic block diagram of a general-purpose computer 400 for practicing the present invention. In FIG. 16, computer system 400 has at least one microprocessor or central processing unit (CPU) 405. CPU 405 is interconnected via a system bus 410 to a random access memory (RAM) 415, a read-only memory (ROM) 420, an input/output (I/O) adapter 425 for a connecting a removable data and/or program storage device 430 and a mass data and/or program storage device 435, a user interface adapter 440 for connecting a keyboard 445 and a mouse 450, a port adapter 455 for connecting a data port 460 and a display adapter 465 for connecting a display device 470.

ROM 420 contains the basic operating system for computer system 400. The operating system may alternatively reside in RAM 415 or elsewhere as is known in the art. Examples of removable data and/or program storage device 430 include magnetic media such as floppy drives and tape drives and optical media such as CD ROM drives. Examples of mass data and/or program storage device 435 include hard disk drives and non-volatile memory such as flash memory. In addition to keyboard 445 and mouse 450, other user input devices such as trackballs, writing tablets, pressure pads, microphones, light pens and position-sensing screen displays may be connected to user interface 440. Examples of display devices include cathode-ray tubes (CRT) and liquid crystal displays (LCD).

A computer program with an appropriate application interface may be created by one skilled in the art and stored on a system or a data and/or program storage device to simplify the practicing of this invention. In operation, information for or the computer program created to run the present invention is loaded on the appropriate removable data and/or program storage device 430, fed through data port 460 or typed in using keyboard 445. In a first example, the output of the system bus 410 may control the apparatuses 100 and 200 of FIGS. 1, 2A and 2B) and methods 600 and 700 of FIGS. 3A and 3B, respectively, resulting in containing and isolating PCB-contaminated sediments while they may be being handled with the rate of suspension and turbidity of the sediments being controlled. In a second example, the output of the system bus 410 may control the apparatuses 100 and 200 enabling sampling, viewing, sonar detection, monitoring, separating, testing, treating, injecting, removing or replacing contaminated materials from a contained site within a body of water.

The present invention can provide a structure e.g., the apparatuses 100 and 200 of FIGS. 1, 2A and 2B) and methods 600 and 700 of FIGS. 3A and 3B, respectively, for containing and isolating the PCB-contaminated sediments while they may be handled and the rate of suspension and turbidity of the sediments may be controlled. The apparatuses 100 and 200 enabling sampling, viewing, sonar detection, monitoring, separating, testing, treating, injecting, removing or replacing contaminated materials from a contained site within a body of water. The open faced vessels 110 and 210 form a sealable/resealable container with the bottom materials, then uses "agitators" for suspending contaminated material such as silt and sludge within the container and outlets through which a mixture of the materials and fluids may be withdrawn from the vessel for separation and monitoring for chemicals and/or treatment. Most PCBs reside in the top 6 inches of the sediment layer at the bottom of the river. However, at some hot spots, PCBs may be present at a depth as deep as 25 inches. The "agitators" will be variable speed impellers, whips and nozzles for directing a stream of water or air at variable pressures. The container, agitators, impellers, whips and nozzles may be of mixed materials, for example: carbon steel, aluminum, stainless steel, rubber, plastic or composites.

A global positioning device (GPD) can be used to determine the positioning of the vessels 110 and 210. Also, the open or closed loop piping system 188 may include a "forward and reverse" pump 380 for removing the contaminated material such as silt and sludge materials from attachment 248" and from piping system 45 of apparatus 100, as depicted in FIG. 1, and piping system 188 of apparatus 200, as depicted in FIG. 2A, supra, while the releasable seal 183 prevents contaminated material from entering the vessels 110 or 210. Monitoring the sample site 310a, as depicted in FIG. 2B, may include testing for chemicals and elements known or unknown. The treatments can include using additives, reducers, catalysts, microbes, stabilizers, adhesives, charged particles, gases or other elements known or unknown. Once treated, "cleaned, separated materials" may be returned via the open or closed piping system 188, as depicted in FIG. 2A or the closed loop piping system 45, as depicted in FIG. 1. The apparatuses 100 and 200 enables removal of contaminated materials "in place" with continuous monitoring and minimal exposure to the surroundings.

The apparatuses 100 and 200 have the following advantages over the conventional dredging method that may use the "open mouthed" bucket. First, the apparatuses 100 and 200 may have a multi-use purpose, such as, for example, sampling, viewing, sonar detection, monitoring, separating, testing, treating, injecting, removing or replacing contaminated material from a contained site within the riverbed. Second, the "open or closed loop" piping systems 188 within the containment vessel area may be used to stimulate and control the rate of suspension of materials (turbidity) and the depth of involvement into the riverbed materials as well. The agitators may be variable speed impellers 125a and 125b, whip 127 or nozzles 135a, 135b, 135c, 135d and may be adapted for rising up and down, while advancing into the contaminated material such as sediment 270, e.g., silt and sludge media, to a controlled depth. Third, the apparatuses 100 and 200 may be a multiple "closed looped" or "open loop" piping systems, 45 and 188 that recycle the enclosed fluids out of the vessels 110 and 210 and back into the vessels 110 and 210, enabling elected treatments or filtration processes. Fourth, testing and treatments to the contained sediment 78 and 270, e.g., silt and sludge media, can be done in place in the vessels 110 and 210 in lieu of removing it from the vessels 110 and 210. Fifth, by reversing the process the voids left from removals can be filled with a selected amount of cleaned or new fill materials such as plant life and organisms, etc.

Direct benefits to using the apparatuses 100 and 200 may be seen with respect to working below the mud line with quiet, night-and-day, year-round operations and minimal effects to the river, navigation, public water supplies, improving the public's health, improving the ecology of the river, the fish and wildlife, the food chain, improved agricultural applications, improved transportation and recreation. There may be several objectives achieved using the apparatuses 100 and 200 of the present invention: (1) reduced cancer risks and non-cancer health hazards to people who eat fish, (2) lowered risks to fish and wildlife, (3) diminished PCB levels in sediments in river water above water quality standards, (4) reduced quantity (mass) of PCBs in sediments that may be consumed by fish and wildlife, and (5) stopped long-term movement of PCBs down the river.

One success of the apparatuses of the present invention, e.g., the apparatuses 100 and 200 of FIGS. 1, 2A and 2B) and methods 600 and 700 of FIGS. 3A and 3B, respectively, can be measured by the minimization of the amount of materials (large rocks, stones, etc.) that may be collected and/or processed for transport to a disposal site.

A second success of the apparatuses of the present invention, e.g., the apparatuses 100 and 200 of FIGS. 1, 2A and 2B) and methods 600 and 700 of FIGS. 3A and 3B, respectively, may be enabling targeting of contaminated materials for removal, so that essentially 100% by weight of the contaminated materials may be removed.

The environmental benefits may be the controlled removal of contaminated materials such as river sediment to prevent downstream migration of the contaminated materials that may result if the contaminated materials were not removed. The present invention may provide economic benefits in the form of returning a body of water such as the Hudson River to safe use again.

The energy benefits of the apparatuses of the present invention, e.g., the apparatuses 100 and 200 of FIGS. 1, 2A and 2B) and methods 600 and 700 of FIGS. 3A and 3B, respectively, may be expected to cut the energy consumption for PCB removal and treatment by a significant amount by shortening the length of the treatment process. The environmental protection may be offered through the novel contained dredging process (i.e., inside the vessel 210) by controlling turbidity and re-suspension released downstream. The economic benefits may be derived from a shortened, safer, more efficient process enabling the economy to regain use of bodies of water such as the Hudson River sooner. The marketing potential to recover contaminated sediments in any body of water throughout New York State, the U.S., and all of the developing countries of the world may be limitless.

The present invention can also provide the means to regenerate plant life and install plant life into a body of water such as a river in efficient and economical ways. According to embodiments of the present invention, plant life may be selected so that it may be able to co-habit together and repopulate the vacant site. Research will be conducted for the nutrients and packets that each habitat may require. The Green Plant Energy Aid System (i.e., the growth packet 900 of FIG. 5), hereafter known as GREEN PEAS, may be a biodegradable packet, filled with plants (cuttings, roots, tubers, seeds, etc.), nutrients, soil, and organisms necessary to accelerate plant growth in a greenhouse growing effect that shelters new growth from the forces of nature over a controlled period of time, aiding in accelerated plant growth. The GREEN PEAS may be prepackaged high-energy growing pods, round in shape, to facilitate easy placement. The shape enables the GREEN PEAS to be pumped via special piping systems into soil whether above or below the waterline as in river bottoms for soil erosion control. It also enables the PEAS not to have a top or a bottom, enabling growth to occur at 360 degrees, thus finding "top" on its own. The GREEN PEAS should also be weighted to sink or air bladdered to float as in hydroponic farming. The GREEN PEAS will be filled with soil and water organisms necessary to restart damaged eco systems such as brown field sites, slag heaps, run off ponds, lagoons, fire sites and harbors.

The benefits of this project may be: the river, improving the public's health, improving the ecology of the body of water, such as providing a healthier environment for the fish and wildlife, eliminating PCB's and other toxic chemicals from the food chain, improving the purity of public water supplies, removing waste from the body of water that may result from agricultural applications, such as the use of fertilizers, and improving conditions for recreation on the body of water such as for swimming. The financial benefits may be boundless for both commercial and public applications.

This present invention may be superior because the direct planting process replants the riverbed with GREEN PEAS. Replacing a controlled amount of material will be far more efficient and cost effective than current procedures used today. The energy and economic benefits may be based upon the savings associated with the efficient way of replanting the river bottom voided of habitat. The direct planting process to replant the river bed and replace a controlled amount of clean material (12" as required by the USEPA) will save a measurable amount of new soil materials over the current methods of transferring or clam shelling the soil material into a flowing river which carries the materials with the current before they settle out unevenly on the bottoms. The environmental benefits to the fish, waterfowl, amphibious and aquatic fauna may be measured by how long it takes to plant the habitat vegetation and replace the ecological functions.

With the GREEN PEAS process, the nutrient rich power pods will jumpstart growing the plants prior to planting in the riverbed. Already able to provide a root area support system, the GREEN PEAS may be placed under the riverbed soils by the mechanical process. This may be unlike current practices that use drop in place techniques in which plant life could be washed away with river currents.

As a summary of the benefits of the present invention, the present invention preserves the quality of life around the site of cleaning operation. The operation of the apparatuses 100 and 200 makes negligible noise, creates no pollution, and generates no smell. Such benefits will be greatly appreciated and welcomed by the public.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

I claim:

1. An apparatus for remediation of contaminated sediment at the bottom of a body of water, said apparatus comprising:
    a vessel having an opening facing and configured for direct physical contact with the bottom of the body of water so as to isolate contaminated locations contained within the opening from locations outside the opening;
    the vessel comprising:
        at least one agitator for suspending sediment contained within the opening;
        an observing device coupled to an interior of the vessel for determining a pre-specified thickness of a top of the contaminated sediment for being suspended in the interior of the vessel;
    a mapping system (40) for determining a longitudinal and latitudinal coordinates of the contaminated locations;
    a pumping system including first pipes configured to transport the contained and suspended sediment from the isolated location.

2. The apparatus of claim 1, wherein the mapping system is a Geographical Positioning System (GPS).

3. The apparatus of claim 2, wherein the at least one agitator is selected from the group consisting of a paddle, an auger, a spray head, a whip, a prop a fluid distribution device and a gas distribution device.

4. The apparatus of claim 1, comprising a processing system for removing contaminants from suspended sediment.

5. The apparatus of claim 4, wherein the processing system comprises a filter system.

6. The apparatus of claim 1, wherein the processing system is configured for a treatment of the suspended sediment selected from the group consisting of, chemical treatment, radiation treatment and a combination thereof.

7. The apparatus of claim 6, further comprising any of:
    a sampling device coupled to the vessel and adapted to sample the materials within the interior of the vessel;
    a lifting device coupled to the vessel and adapted for positioning the vessel; and/or
    a testing system coupled to the vessel and configured to test the materials within the interior of the vessel.

8. The apparatus of claim 1, further comprising a vacuum system coupled to the vessel and configured to reduce the pressure of the interior of the vessel so as to releaseably seal the vessel onto the bottom of the body of water.

9. The apparatus of claim 1, comprising:
    a computer,
        wherein the computer (400) calculates operating parameters for the controlled agitators, viewing equipment, map coordinate locating equipment, and wherein the apparatuses (100) and (200) suspend the pre-specified thickness of the top layer of the contaminated material in the interior of the vessel.

10. The apparatus of claim 1, comprising:
a computer (400) for controlling the apparatuses (100) and (200), including valves, agitators, viewing equipment, and map coordinate locating equipment of the apparatuses (100) and (200), wherein the computer (400) calculates operating parameters for the agitators, viewing equipment, map coordinate locating equipment, and wherein the apparatuses (100) and (200) suspend the pre-specified thickness of the top layer of the contaminated material in the interior of the vessel.

11. The apparatus of claim 1, wherein the observing device is a sonar device or a camera.

12. An apparatus for remediation of contaminated sediment at the bottom of a body of water, said apparatus comprising:
a vessel having an opening facing and configured for direct physical contact with the bottom of the body of water so as to isolate an area contained within the opening from areas outside the opening;
at least one agitator for suspending sediment contained within the opening;
a mapping system (40) for determining a longitudinal and latitudinal coordinates of the locations;
first pipes configured to transport the contained and suspended sediment from the isolated area to the mapping system; and
second pipes configured to transport processed suspended sediment from a processing system to the isolated area, wherein the second pipes are further configured to transport a growth packet containing materials for plant growth into the interior of the vessel.

13. A method for removing chemical contaminants at the bottom of a body of water, comprising:
providing the apparatus as defined in any preceding claim;
positioning the vessel above the contaminated sediment with its opening facing and in direct physical contact with the bottom of the body of water;
agitating the water in the resulting isolated area to suspend sediment contained therein;
transporting the contained and suspended sediment to the processing system, removing contaminants from the suspended sediment by means of the processing system and transporting suspended sediment from the processing system to the isolated area for refilling the isolated area.

14. The method of claim 13, wherein the contaminant is selected from:
(a) mercury, lead or other heavy metal;
(b) chromium, magnesium, manganese or copper;
(c) polychlorinated biphenyl or a chlorinated dioxin;
(d) benzene, toluene, trichloroethylene or another aromatic or halogenated solvent.

15. The method of claim 14, further comprising providing a vacuum system coupled to the vessel and reducing, with the vacuum system, the pressure of the interior of the vessel so as to releaseably seal the vessel onto the bottom of the body of water.

16. The method of claim 15, further comprising providing a sample site coupled to the first pipe, and transporting to the sample site samples of the materials in the first pipe for testing.

17. The method of claim 13, wherein the body of water is naturally occurring and is a lake, reservoir, river or stream.

18. A contaminated material treating system, comprising:
a vessel including an opening,
wherein when the opening is facing a layer of contaminated material on a bottom of a body of water and the opening is in direct physical contact with a top layer of the contaminated material; and
an observing device,
wherein the observing device is operably coupled to an interior of the vessel,
wherein the vessel has been configured to contain and suspend the contaminated material in an interior of the vessel, and
wherein the vessel has been configured to suspend the contaminated material until a pre-specified thickness of the top layer of the contaminated material has been suspended in the interior of the vessel.

19. The system of claim 18, wherein the observing device is configured to determine whether the pre-specified thickness of the top layer of the contaminated material is suspended in the interior of the vessel.

20. The system of claim 18, wherein the observing device is a sonar device or a camera.

21. The system of claim 18, further comprising a first pipe coupled to the vessel and configured to transport treating chemicals to the interior of the vessel.

22. A method for processing contaminated material at a bottom of a body of water, the method, comprising:
providing a vessel including an opening and a observing device coupled to an interior of the vessel;
placing the vessel such that the opening is facing a layer of contaminated material on the bottom of the body of water and in direct physical contact with a top layer of the contaminated material; and
observing and suspending the contaminated material until a pre-specified thickness of the top layer of the contaminated material is suspended in the interior of the vessel.

23. The method of claim 22, further comprising:
determining, with the observing device, whether the pre-specified thickness of the top layer of the contaminated material is suspended in the interior of the vessel.

24. The method of claim 22, wherein the observing device is a sonar device or a camera.

25. The method of claim 22, further comprising:
providing a first pipe coupled to the vessel; and
transporting treating chemicals to the interior of the vessel via the first pipe.

26. The method of claim 22, comprising:
an operator entering map coordinates and a depth of removal for a location where contaminated material has been designated for removal; and
controlling the apparatuses (100 and 200), including valves, agitators, viewing equipment, map coordinate locating equipment of the apparatuses (100 and 200) with a computer (400), wherein the computer (400) calculates operating parameters for the controlled agitators, viewing equipment, map coordinate locating equipment, and
wherein the apparatuses (100 and 200) suspend the pre-specified thickness of the top layer of the contaminated material in the interior of the vessel.

27. The method of claim 26, wherein the map coordinate locating equipment is selected from the group consisting of GPS and Sonar equipment.

* * * * *